(12) United States Patent
Hadwen et al.

(10) Patent No.: US 10,113,985 B2
(45) Date of Patent: Oct. 30, 2018

(54) ACTIVE MATRIX DEVICE AND METHOD OF DRIVING

(71) Applicant: Sharp Life Science (EU) Limited, Oxford (GB)

(72) Inventors: Benjamin James Hadwen, Oxford (GB); Christopher James Brown, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 452 days.

(21) Appl. No.: 14/854,626

(22) Filed: Sep. 15, 2015

(65) Prior Publication Data

US 2017/0074814 A1    Mar. 16, 2017

(51) Int. Cl.
| | | |
|---|---|---|
| *G01N 27/02* | (2006.01) | |
| *B01L 3/00* | (2006.01) | |
| *G01N 15/00* | (2006.01) | |

(52) U.S. Cl.
CPC ........ *G01N 27/028* (2013.01); *B01L 3/50273* (2013.01); *B01L 3/502792* (2013.01); *G01N 15/00* (2013.01); *B01L 2300/024* (2013.01); *B01L 2300/0645* (2013.01); *B01L 2300/0819* (2013.01); *B01L 2400/0427* (2013.01)

(58) Field of Classification Search
None
See application file for complete search history.

(56) References Cited

U.S. PATENT DOCUMENTS

| | | | |
|---|---|---|---|
| 6,565,727 | B1 | 5/2003 | Shenderov |
| 6,911,132 | B2 | 6/2005 | Pamula et al. |
| 7,163,612 | B2 | 1/2007 | Sterling et al. |
| 8,653,832 | B2 | 2/2014 | Hadwen et al. |
| 2012/0194492 | A1* | 8/2012 | Hadwen ............... B01L 3/50273 345/207 |

FOREIGN PATENT DOCUMENTS

EP    2404675    1/2012

OTHER PUBLICATIONS

"Digital microfluidics: is a true lab-on-a-chip possible?", R.B. Fair, Microfluid Nanofluid (2007) 3:245-281).

* cited by examiner

*Primary Examiner* — Eli S Mekhlin
(74) *Attorney, Agent, or Firm* — Renner, Otto, Boisselle & Sklar, LLP

(57) ABSTRACT

An active matrix electro-wetting on dielectric (AM-EWOD) device includes a plurality of array elements arranged in an array, each array element including array element circuitry, an element electrode, and a reference electrode. The array element circuitry includes an actuation circuit configured to apply actuation voltages to the electrodes, and an impedance sensor circuit configured to sense impedance at the array element electrode to determine a droplet property. The actuation circuitry includes a memory capacitor for storing voltage data corresponding to either an actuated state or an unactuated state of the array element, and an input applied to the memory capacitor operates to effect an operation of the impedance sensor circuit. Such input may isolate the array element from the actuation voltage during operation of the impedance sensor circuit, and the memory capacitor may operate as part of the impedance sensor circuit as a reference capacitor for determining the droplet property.

12 Claims, 21 Drawing Sheets

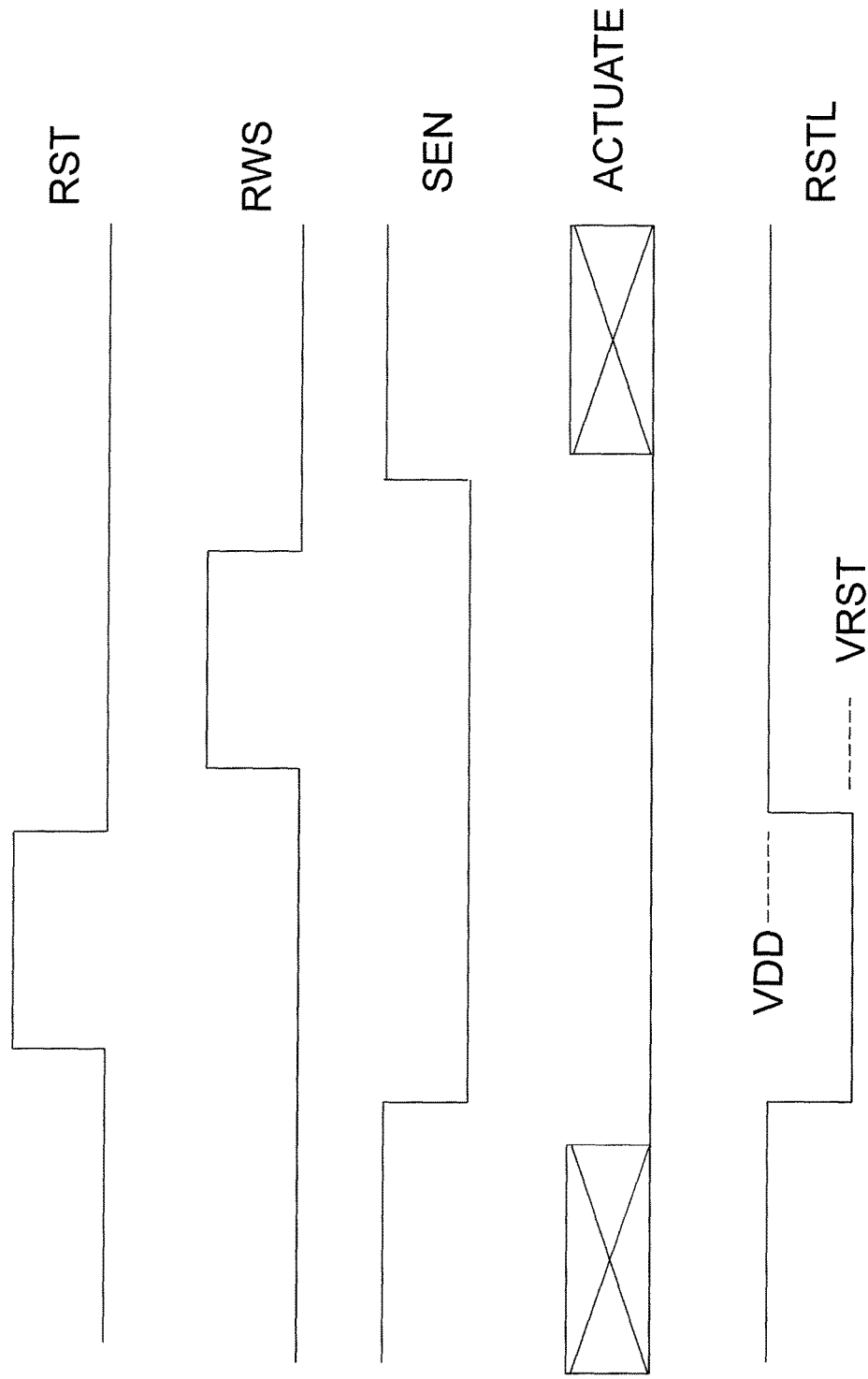

ACTIVE MATRIX DEVICE AND METHOD OF DRIVING

TECHNICAL FIELD

The present invention relates to active matrix arrays and elements thereof. In a particular aspect, the present invention relates to digital microfluidics, and more specifically to Active Matrix Electro-wetting-On-Dielectric (AM-EWOD), and further relates to methods of driving such a device.

BACKGROUND ART

Electro-wetting on dielectric (EWOD) is a well known technique for manipulating droplets of fluid by application of an electric field. Active Matrix EWOD (AM-EWOD) refers to implementation of EWOD in an active matrix array incorporating transistors, for example by using thin film transistors (TFTs). It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 72, the uppermost layer of which is formed from a conductive material which is patterned so that a plurality of array element electrodes 38 (e.g., 38A and 38B in FIG. 1) are realized. The electrode of a given array element may be termed the array element electrode 38. The liquid droplet 4, comprising a polar material (which is commonly also aqueous and/or ionic), is constrained in a plane between the lower substrate 72 and a top substrate 36. A suitable gap between the two substrates may be realized by means of a spacer 32, and a non-polar fluid 34 (e.g. oil) may be used to occupy the volume not occupied by the liquid droplet 4. An insulator layer 20 disposed upon the lower substrate 72 separates the conductive element electrodes 38A, 38B from a first hydrophobic coating 16 upon which the liquid droplet 4 sits with a contact angle 6 represented by θ. The hydrophobic coating is formed from a hydrophobic material (commonly, but not necessarily, a fluoropolymer).

On the top substrate 36 is a second hydrophobic coating 26 with which the liquid droplet 4 may come into contact. Interposed between the top substrate 36 and the second hydrophobic coating 26 is a reference electrode 28.

The contact angle θ 6 is defined as shown in FIG. 1, and is determined by the balancing of the surface tension components between the solid-liquid ($\gamma_{SL}$), liquid-gas ($\gamma_{LG}$) and non-polar fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \quad \text{(equation 1)}$$

In certain cases, the relative surface tensions of the materials involved (i.e the values of $\gamma_{SL}$, $\gamma_{LG}$ and $\gamma_{SG}$) may be such that the right hand side of equation (1) is less than −1. This may commonly occur in the case in which the non-polar fluid 34 is oil. Under these conditions, the liquid droplet 4 may lose contact with the hydrophobic coatings 16 and 26, and a thin layer of the non-polar fluid 34 (oil) may be formed between the liquid droplet 4 and the hydrophobic coatings 16 and 26.

In operation, voltages termed the EW drive voltages, (e.g. $V_T$, $V_0$ and $V_{00}$ in FIG. 1) may be externally applied to different electrodes (e.g. reference electrode 28, array element electrodes 38, 38A and 38B, respectively). The resulting electrical forces that are set up effectively control the hydrophobicity of the hydrophobic coating 16. By arranging for different EW drive voltages (e.g. $V_0$ and $V_{00}$) to be applied to different element electrodes (e.g. 38A and 38B), the liquid droplet 4 may be moved in the lateral plane between the two substrates 72 and 36.

In the following description, it will be assumed that an element of an EWOD device, such as the device of FIG. 1, may receive "digital" data so that the element is required to be put in either an "actuated" state in which the voltage applied across the element is sufficient for a liquid droplet in the element (if one is present in the element) to experience a significant electro-wetting force, or a "non-actuated" state in which the voltage applied across the element is not sufficient for a liquid droplet in the element (if one is present in the element) to experience a significant electro-wetting force. An element of an EWOD device may be put into the actuated state by applying a voltage difference across the EWOD element having a magnitude that is equal to, or greater than, a threshold voltage $V_{EW}$, whereas if the voltage difference across the EWOD element has a magnitude that is less than the threshold voltage $V_{EW}$ the element is in its non-actuated state. The threshold voltage $V_{EW}$ is often referred to as an "actuation voltage", and this term is used below. In practice, the threshold voltage may typically be determined as the minimum voltage required to effect droplet operations, for example the moving or splitting of droplets. In practice, the non-actuated state may typically be zero volts. Typically EWOD systems may be considered to be digital, in that the EWOD elements are programmed either to an actuated or non-actuated state. It should however be understood that an EWOD device may also be operated by supplying analogue data, such that EWOD elements may be partially actuated.

U.S. Pat. No. 6,565,727 (Shenderov, issued May 20, 2003) discloses a passive matrix EWOD device for moving droplets through an array.

U.S. Pat. No. 6,911,132 (Pamula et al., issued Jun. 28, 2005) discloses a two dimensional EWOD array to control the position and movement of droplets in two dimensions.

U.S. Pat. No. 6,565,727 further discloses methods for other droplet operations including the splitting and merging of droplets, and the mixing together of droplets of different materials.

U.S. Pat. No. 7,163,612 (Sterling et al., issued Jan. 16, 2007) describes how TFT based thin film electronics may be used to control the addressing of voltage pulses to an EWOD array by using circuit arrangements similar to those employed in Active Matrix (AM) display technologies.

The approach of U.S. Pat. No. 7,163,612 may be termed "Active Matrix Electro-wetting on Dielectric" (AM-EWOD). There are several advantages in using TFT based thin film electronics to control an EWOD array, namely:

Electronic driver circuits can be integrated onto the lower substrate 72.

TFT-based thin film electronics are well suited to the AM-EWOD application. They are cheap to produce so that relatively large substrate areas can be produced at relatively low cost.

TFTs fabricated in standard processes can be designed to operate at much higher voltages than transistors fabricated in standard CMOS processes. This is significant since many EWOD technologies require EWOD actuation voltages in excess of 20V to be applied.

A disadvantage of U.S. Pat. No. 7,163,612 is that it does not disclose any circuit embodiments for realizing the TFT backplane of the AM-EWOD.

EP2404675 (Hadwen et al., published Jan. 11, 2012) describes array element circuits for an AM-EWOD device. Various methods are known for programming and applying an EWOD actuation voltage to the EWOD element electrode. The programming function described includes a memory element of standard means, for example, based on Dynamic RAM (DRAM) or Static RAM (SRAM) and input lines for programming the array element.

Whilst EWOD (and AM-EWOD) devices can be operated with either DC or AC actuation voltages, in practice there are many reasons for preferring an AC method of driving, as reviewed in the previously cited reference R. B. Fair, Microfluid Nanofluid (2007) 3:245-281). It may be noted that droplets can be actuated and manipulated for a wide range of AC driving frequencies ranging typically from a few hertz to several kHz.

U.S. Pat. No. 8,653,832 (Hadwen et al., issued Feb. 18, 2014) describes how an impedance (capacitance) sensing function can be incorporated into the array element. The impedance sensor may be used for determining the presence and size of liquid droplets present at each electrode in the array.

UK Application GB1500261.1, which is herein incorporated by reference, describes a two transistor (2T) array element circuit and a method of driving for implementing an AC driving method of driving. The 2T array element actuation circuit disclosed is shown in FIG. 2 of the current application. This UK application further includes an embodiment showing how the impedance (capacitance) sensing function of U.S. Pat. No. 8,653,832 can be combined with the 2T array element actuation circuit. The array element circuit including the sensor function is shown in FIG. 3 and contains a total of 5 transistors, 3 capacitors and 9 addressing lines. Addressing lines DATA and ENABLE control access to a Dynamic RAM memory circuit comprising the transistor to which they are connected and a capacitor. The voltage programmed to this capacitor in turn controls whether or not the input signal ACTUATE is connected through to an array element electrode. The input signal SEN may further be used to isolate the element electrode from the ACTUATE signal when the sensor is being operated. The sensor function is controlled by two voltage signals applied to terminals RWS and RST. The voltage signal applied to RST resets the voltage at the gate of a sense transistor (connected between VDD and COL) to a reset potential VRST. The voltage signal applied to RWS perturbs the voltage at the element electrode by an amount dependent on the ratio of the fixed capacitors in the circuit present at the element electrode and the capacitance presented by the presence or absence by a liquid droplet at the element electrode. A voltage signal is thus coupled to the gate of the sensing transistor which is converted to an output current through COL. The impedance presented at the element electrode may thus be measured.

SUMMARY OF INVENTION

A first aspect of the invention provides an array element circuit and method of driving an element of an active matrix electro-wetting on dielectric (AM-EWOD) device, the AM-EWOD element having an element electrode and a reference electrode.

The method comprises actuation of a liquid droplet which may be present at the location of the array element and also the sensing of the impedance associated with a droplet, or the absence of a droplet, at the location of the array element.

The method of droplet actuation is comprised of applying a first alternating voltage to the reference electrode; and either applying to the element electrode a second alternating voltage that has the same frequency as the first alternating voltage and that is out of phase with the first alternating voltage or holding the element electrode in a high impedance state.

The "high impedance state" refers to an impedance between the element electrode and ground that is of the order of at least 100 Mega-ohm. The "high impedance state" may have an impedance between the element electrode and ground that is of the order of at least 1 Giga-ohm.

When the second alternating voltage is applied to the element electrode, the element is put in an actuated state in which the element is configured to actuate any liquid droplet present in the element, while when the element electrode is held in the high impedance state the element is put in a non-actuated state.

The array element circuit contains a memory function for storing programmed data in accordance with which the array element is configured into an actuated or non-actuated state. The memory function may comprise a dynamic RAM circuit, whereby the programmed information is stored as a voltage programmed onto a storage capacitor.

The method of sensing the impedance may comprise applying a voltage signal so as to perturb the potential of the element electrode, the perturbation being a function of the impedance presented at the element electrode. The method of sensing the impedance may comprise comparing the impedance presented at the element electrode with a reference impedance in the array element circuit.

The storage capacitor (used for storing the programmed actuation state) may further participate in the sensing function of the array element circuit.

According to a first aspect of the invention, the storage capacitor may participate in the sensing function by perturbing the bias at a node of the circuit, in accordance with the application of a voltage signal. Further according to this aspect of the invention, the storage capacitor may effect the perturbing of a bias such as to disconnect an actuation voltage signal from the element electrode during the operation of the sensor circuit.

According to a second aspect of the invention, the storage capacitor may participate in the sensing function by acting as a reference impedance with which the impedance present at the element electrode may be compared during the operation of the sensor circuit.

The AM-EWOD device may comprise a plurality of AM-EWOD elements arranged in a matrix of rows and columns, and wherein the method may comprise arranging for an instantaneous value of the second alternating voltage applied to a row of AM-EWOD elements to be equal to an instantaneous value of the first alternating voltage at a time of putting the element electrodes of AM-EWOD elements of the row into the high impedance state.

The advantages of the invention include:
By driving the AM-EWOD device in this way, AC electro-wetting is achieved, with the electro-wetting voltage being switched between $+V_{EW}$ and $-V_{EW}$ whilst the transistors in the array element circuit are only required to switch a maximum voltage of $V_{EW}$.
This method of driving may be implemented in circuitry requiring a minimal number of transistors (embodiments disclosed include a 2-Transistor array element circuit). Advantages of small array element circuits are:

The size of the array element is minimized. This in turn facilitates larger format arrays, and also the manipulation of smaller liquid droplets.

Smaller/simpler circuits generally facilitate higher manufacturing yield.

Smaller/simpler circuits may facilitate a device arrangement that has a higher optical transparency, the thin film electronics being only partially transparent. Optical transparency may be important in performing chemical tests which involve a change in the optical properties of the liquid droplet which is then measured.

Embodiments of the invention can be realized requiring only n-type (or only p-type) transistors in the array element circuit. The AM-EWOD device can thus be fabricated in a single channel transistor manufacturing process.

BRIEF DESCRIPTION OF DRAWINGS

In the annexed drawings, like references indicate like parts or features:

FIG. 21 is a timing diagram showing an exemplary arrangement of the timing signals for driving the array elements of the exemplary AM-EWOD device of FIG. 4 according to a sixth embodiment of the invention.

Figure 1:
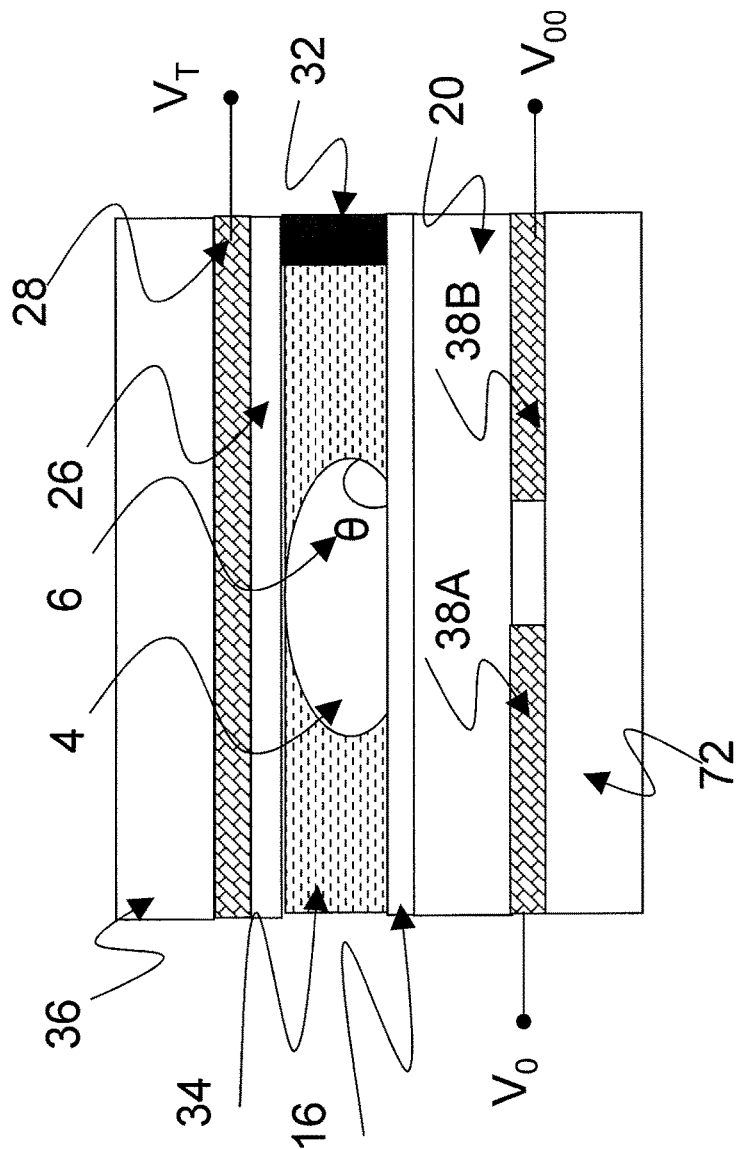
FIG. 1 shows prior art, particularly a schematic diagram depicting a conventional EWOD device in cross-section.
Figure 2:
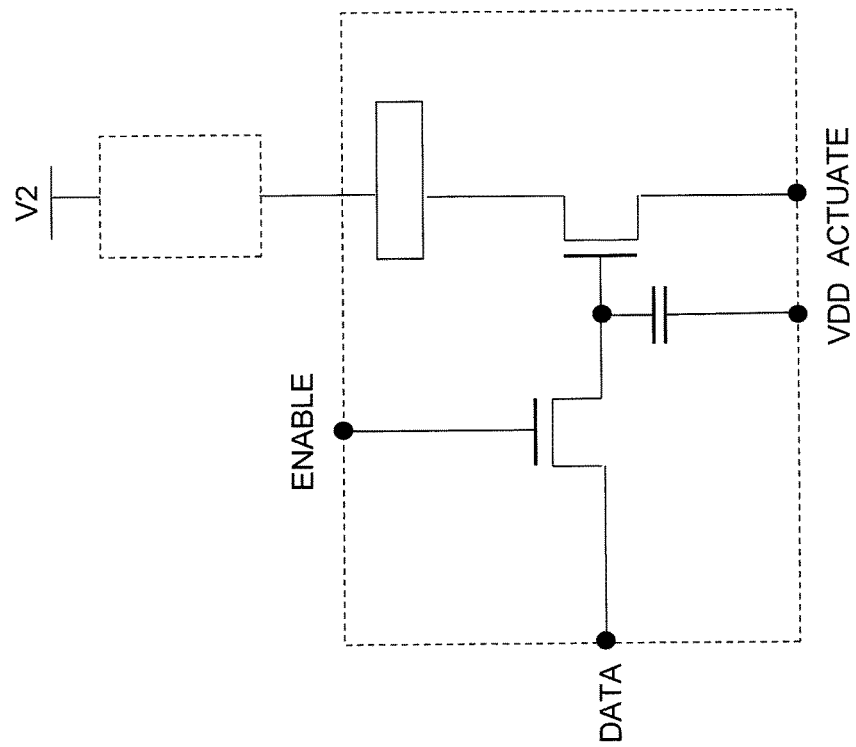
FIG. 2 shows prior art, particularly a 2-transistor AM-EWOD array element actuation circuit

DESCRIPTION OF REFERENCE NUMERALS 4 liquid droplet
6 contact angle θ
16 First hydrophobic coating
20 Insulator layer
26 Second hydrophobic coating
28 Reference electrode
32 Spacer
34 Non-polar fluid
36 Top substrate
38/38A and 38B Array Element Electrodes
40/40A/40B Electrical load
42 Electrode array
44 Reference capacitor
46 Actuation circuit
48 Sensor circuit
52 Transistor
54 Transistor
56 Memory capacitor
58 Transistor
60 Sensor capacitor
62 Sensing Transistor
64 Transistor
66 Transistor
72 Lower Substrate
74 Thin film electronics
76 Row driver circuit
78 Column driver circuit
80 Serial interface
82 Connecting wires
83 Voltage supply interface
84 Array element circuit
86 Column detection circuit
88 Sensor row addressing

DETAILED DESCRIPTION OF INVENTION

Figure 4:
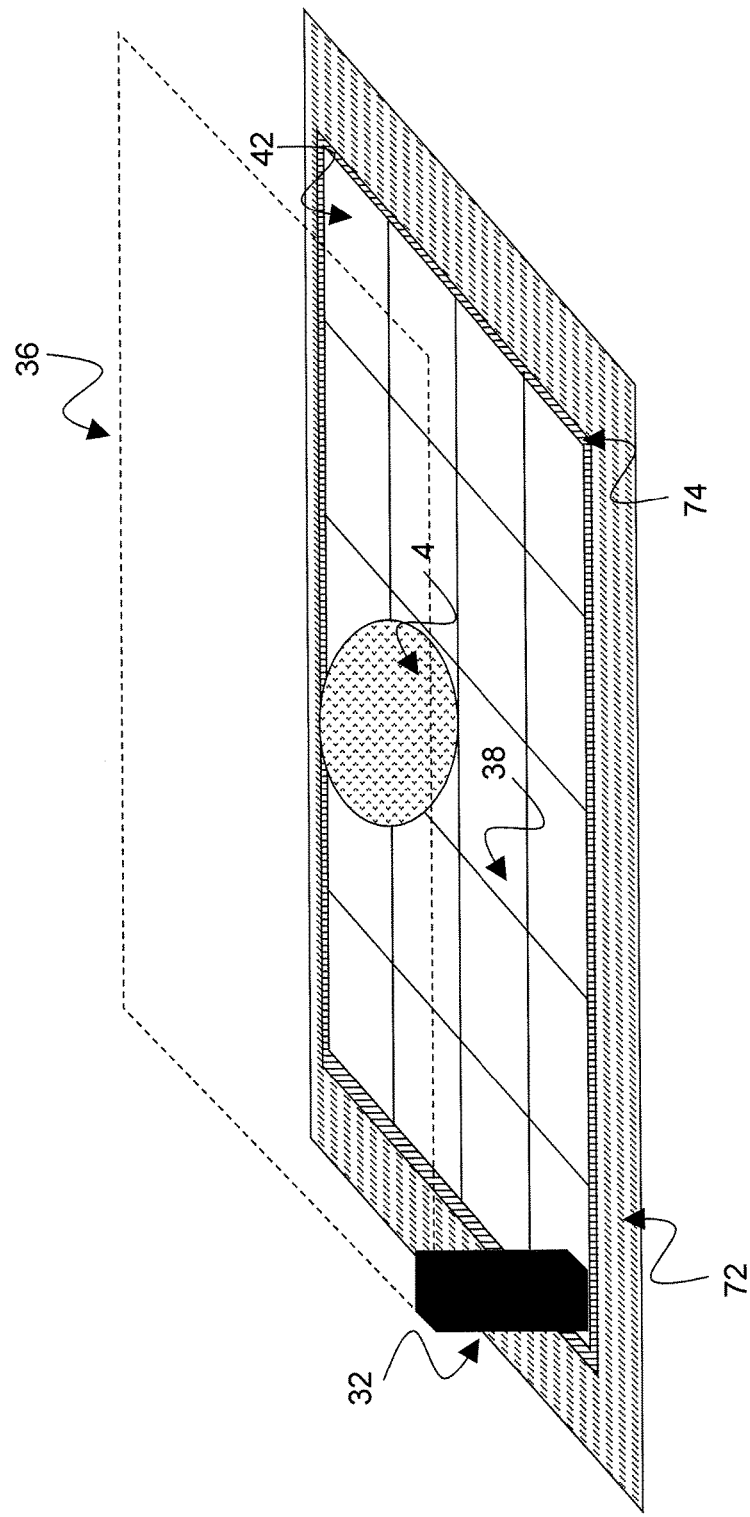
FIG. 4 is a schematic diagram depicting a an AM-EWOD device in schematic perspective in accordance with a first and exemplary embodiment of the invention.

FIG. 4 is a schematic diagram depicting an AM-EWOD device in accordance with an exemplary embodiment of the present invention. The AM-EWOD device has a lower substrate 72 with thin film electronics 74 disposed upon the lower substrate 72. The thin film electronics 74 are arranged to drive the array element electrodes 38. A plurality of array element electrodes 38 are arranged in an electrode array 42, having X by Y elements where X and Y may be any integer. A liquid droplet 4, which may comprise any polar liquid and which typically may be ionic and/or aqueous in nature, is enclosed between the lower substrate 72 and a top substrate 36, although it will be appreciated that multiple liquid droplets 4 can be present. A non-polar fluid 34 is used to fill the space between the substrates and may comprise an oil (for example n-dodecane, silicone oil or other alkane oil) or may be air.

Figure 5:
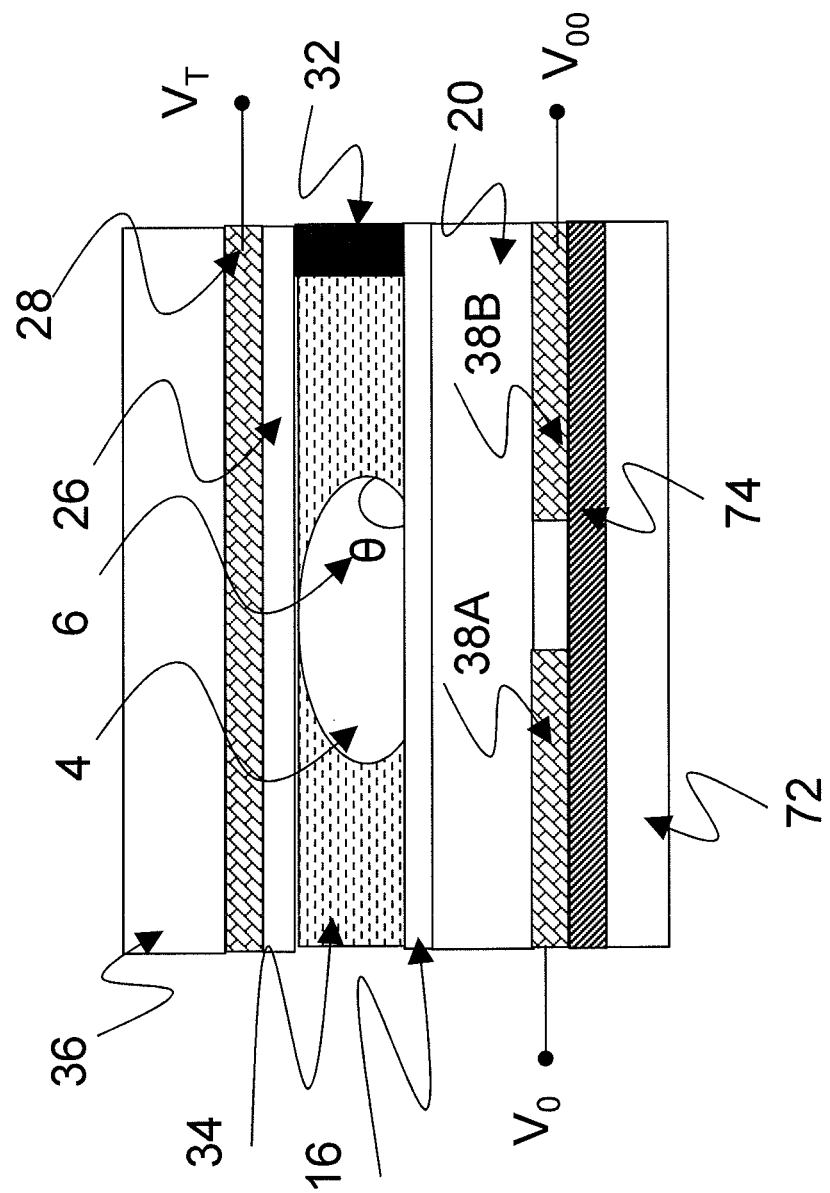
FIG. 5 shows a cross section through some of the array elements of the exemplary AM-EWOD device of FIG. 4.

FIG. 5 is a schematic diagram depicting a pair of the array element electrodes 38A and 38B in cross section that may be utilized in the AM-EWOD device of FIG. 4. The device configuration is similar to the conventional configuration shown in FIG. 1, with the AM-EWOD device further incorporating the thin-film electronics 74 disposed on the lower substrate 72. The uppermost layer of the lower substrate 72 (which may be considered a part of the thin film electronics layer 74) is patterned so that a plurality of the array element electrodes 38 (e.g. specific examples of element electrodes are 38A and 38B in FIG. 5) are realized. These may be termed the array element electrodes 38. The term array element electrode 38 may be taken in what follows to refer both to the physical electrode structure 38 associated with a particular array element, and also to the node of an electrical circuit directly connected to this physical structure. The reference electrode 28 is shown in FIG. 5 disposed upon the top substrate, but may alternatively be disposed upon the lower substrate 72 to realize an in-plane reference electrode 28 geometry. The term reference electrode 28 may also be taken in what follows to refer to both or either of the physical electrode structure and also to the node of an electrical circuit directly connected to this physical structure. The electro-wetting voltage may be defined as the difference in voltage between the element electrode 38 and the reference electrode 28.

Figure 6:
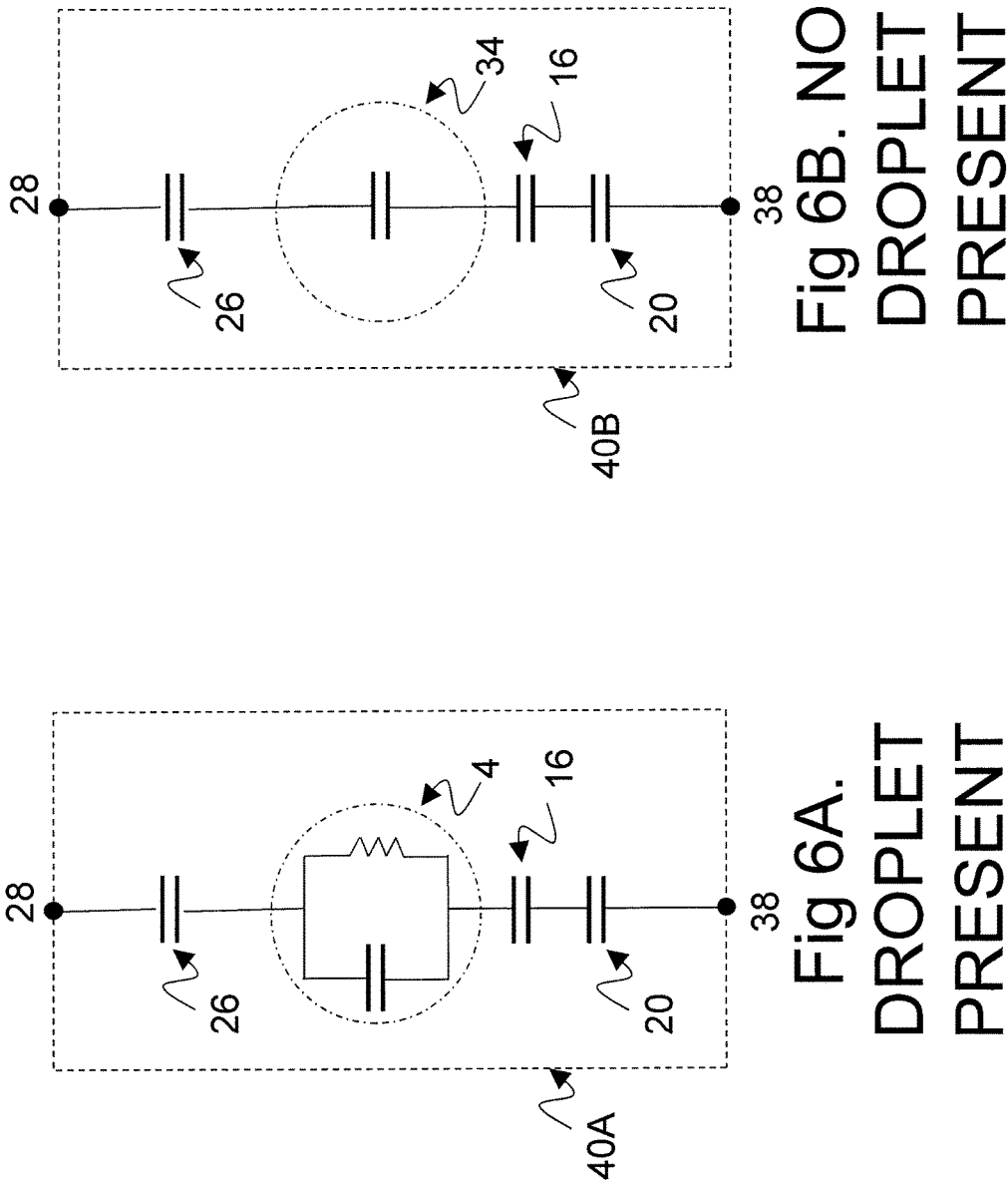
FIG. 6A shows a circuit representation of the electrical load presented at the element electrode when a liquid droplet is present.
FIG. 6B shows a circuit representation of the electrical load presented at the element electrode when no liquid droplet is present.

FIG. 6A shows a circuit representation of the electrical load 40A between the element electrode 38 and the reference electrode 28 in the case where a liquid droplet 4 is present. The liquid droplet 4 can usually be modelled as a resistor and capacitor in parallel. Typically the resistance of the droplet will be relatively low (e.g. if the droplet contains ions) and the capacitance of the droplet will be relatively high (e.g. because the relative permittivity of polar liquids is relatively high, e.g. ~80 if the liquid droplet is aqueous). In many situations the droplet resistance is relatively small and so, at the frequencies of interest for electro-wetting, the liquid droplet 4 may function in effect as an electrical short circuit. The hydrophobic coatings 16 and 26 have electrical characteristics that may be modelled as capacitors, and the insulator 20 may also be modelled as a capacitor. The overall impedance between the element electrode 38 and the reference electrode 28 may be approximated by a capacitor whose value is typically dominated by the contribution of the insulator 20 and hydrophobic coatings 16 and 26 contributions, and which for typical layer thicknesses and materials may be of order a pico-Farad in value. The overall value of the electrical load 40A when a liquid droplet 4 completely covers the element electrode 38 may be denoted as $C_T$.

FIG. 6B shows a circuit representation of the electrical load 40B between the element electrode 38 and the reference electrode 28 in the case where no liquid droplet 4 is present. In this case the liquid droplet 4 components are replaced by a capacitor representing the capacitance of the non-polar fluid 34 which occupies the space between the top and lower substrates. In this case the overall impedance between the element electrode 38 and the reference electrode 28 may be approximated by a capacitor whose value is dominated by the capacitance of the non-polar fluid and which is typically small, of order femto-Farads. The overall value of the electrical load 40B when there is no liquid droplet 4 present at the element electrode 38 may be denoted as $C_{OIL}$.

For the purposes of driving and sensing, the electrical load 40A/40B overall functions in effect as a capacitor, whose value depends on whether a liquid droplet 4 is present or not at a given element electrode 38. In the case where a droplet is present, the capacitance is relatively high (typically of order pico-Farads) whereas if there is no liquid droplet 4 present the capacitance is low (typically of order femto-Farads). If a droplet partially covers a given electrode 38 then the capacitance may approximately represent the extent of coverage of the element electrode 38 by the liquid droplet 4.

Figure 7:
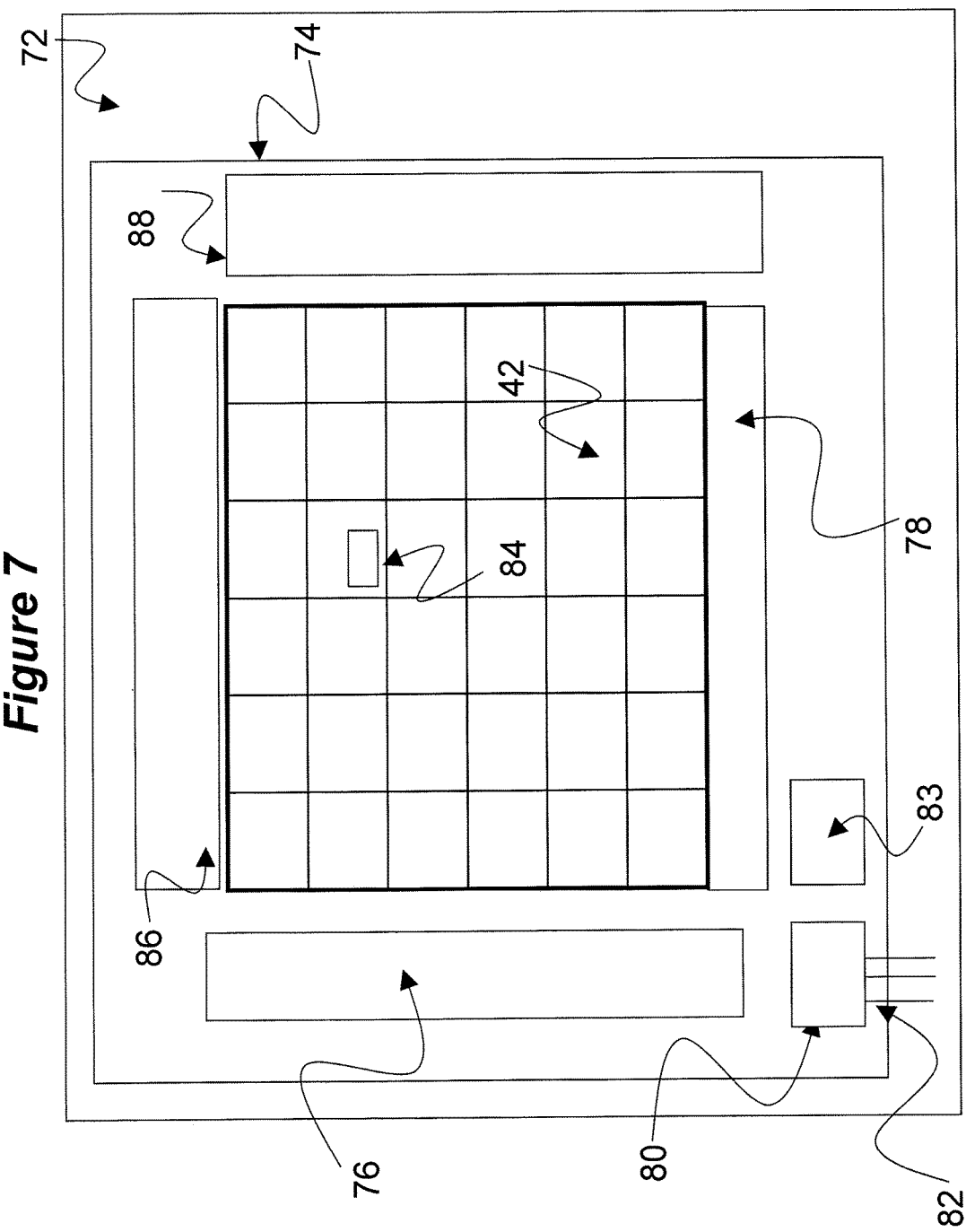
FIG. 7 is a schematic diagram depicting the arrangement of thin film electronics in the exemplary AM-EWOD device of FIG. 4 according to a first embodiment of the invention.

FIG. 7 is a schematic diagram depicting an exemplary arrangement of thin film electronics 74 upon the lower substrate 72 in plan view. Each element of the electrode array 42 contains an array element circuit 84 for controlling the electrode potential of a corresponding element electrode 38 and sensing the impedance present at the electrode 38. Integrated row driver circuit 76 and column driver circuit 78 are also implemented in thin film electronics 74 to supply control signals to the array element circuit 84.

A serial interface 80 may also be provided to process a serial input data stream and facilitate the programming of the required voltages to the element electrodes 38 in the array 42. A voltage supply interface 83 provides the corresponding supply voltages, top substrate drive voltages, and other requisite voltage inputs as further described herein. The number of connecting wires 82 between the lower substrate 72 and external drive electronics, power supplies, and other components can be made relatively few, even for large array sizes. Optionally the serial data input may be partially parallelized, for example if two data input lines are used the first may supply data for columns 1 to X/2 and the second for columns (1+X/2) to X with minor modifications to the column driver circuit 78. In this way the rate at which data can be programmed to the array is increased, which is a standard technique used in Liquid Crystal Display driving circuitry.

The thin film electronics also contains additionally sensor row addressing circuitry 88 for supplying control signals to the sensor circuit inputs (e.g. RW) of the array element circuit 84, and column detection circuits 86 for processing and reading out the output signals from the sensor circuit part of the array element circuit 84.

Generally, an exemplary AM-EWOD device that includes thin film electronics 74 is configured as follows. The AM-EWOD device includes a reference electrode 28 (which, optionally, could be an in-plane reference electrode 28) and a plurality of array elements, each array element including an array element electrode (e.g., array element electrodes 38).

Relatedly, the AM-EWOD device is configured to perform a method of controlling an actuation voltage to be applied to a plurality of array elements. The AM-EWOD device includes reference electrode 28 and a plurality of array elements, each array element including an array element electrode 38. The actuation voltage at each array element is defined by a potential difference between the array element electrode 38 and the reference electrode 28. The method of controlling the actuation voltage includes the steps of supplying a voltage to at least a portion of the array element electrodes 38, and supplying a voltage signal to the reference electrode 28.

Relatedly, the AM-EWOD device is further configured to perform a method of sensing the impedance present at a plurality of array elements. Typically this may involve sensing the impedance at a plurality of array element electrodes, with this impedance being a function of the number, size, position and constitution of one or more liquid droplets 4 present within the array.

In general, therefore, an aspect of the invention is an active matrix electro-wetting on dielectric (AM-EWOD) device. In exemplary embodiments, the AM-EWOD device includes a plurality of array elements arranged in an array of rows and columns, each of the array elements including array element circuitry, an element electrode, and a reference electrode. The array element circuitry includes an actuation circuit configured to apply actuation voltages to the element and reference electrodes for actuating the array element, and an impedance sensor circuit configured to sense impedance at the array element electrode to determine a droplet property at the array element. The actuation circuitry includes a memory part including a memory capacitor for storing voltage data corresponding to either an actuated state or an unactuated state of the array element, and an input applied to the memory capacitor operates to effect an operation of the impedance sensor circuit. In one circuit configuration, the input applied to the memory capacitor operates to isolate the array element from the actuation voltage during the operation of the impedance sensor circuit. In another circuit configuration, the memory circuit alternatively or additionally operates as a reference capacitor in the impedance sensor circuit.

Another aspect of the invention is a corresponding method of operating an active matrix electro-wetting on dielectric (AM-EWOD) device including the steps of: arranging a plurality of array elements in an array of rows and columns, each of the array elements including array element circuitry, an element electrode, and a reference electrode, and the array element circuitry comprises an actuation circuit and an impedance sensor circuit; applying actuation voltages with the actuation circuit to the element and reference electrodes to actuate the array element; wherein the actuation circuitry comprises a memory part including a memory capacitor, the method further comprising for storing voltage data on the memory capacitor corresponding to either an actuated state or an unactuated state of the array element; applying an input to the memory capacitor that operates to effect an operation of the impedance sensor circuit; sensing impedance at the array element electrode with the impedance sensor circuit; and determining a droplet property at the array element based on the sensed impedance. The input to the memory capacitor may effect an operation of the impedance sensor circuit by isolating the array element from the actuation voltage during the operation of the impedance sensor circuit, and/or the input to the memory capacitor effects an operation of the impedance sensor circuit by operating as a reference capacitor in the operation of the impedance sensor circuit.

Figure 8:
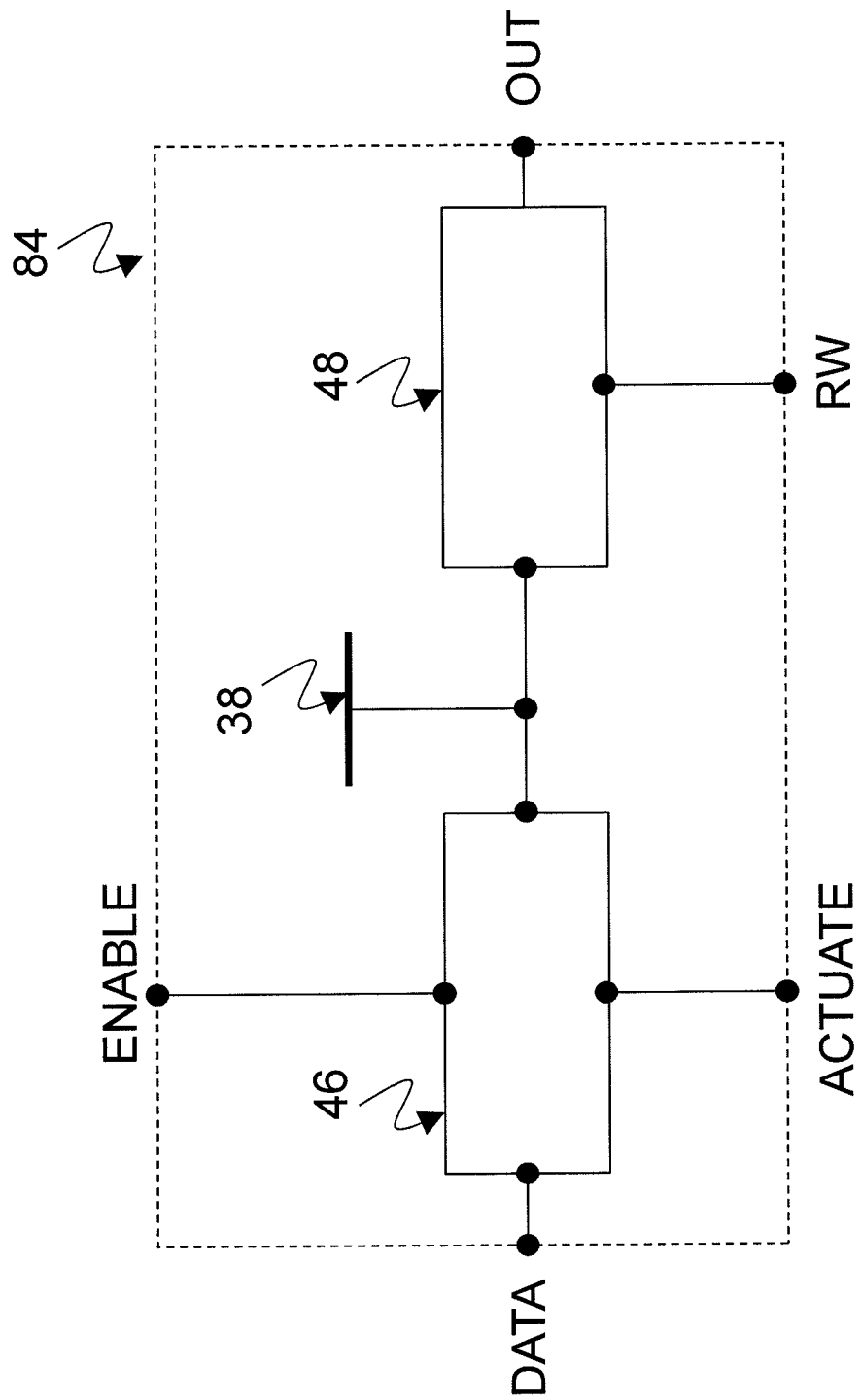
FIG. 8 shows a schematic arrangement of the array element circuit in accordance with a first embodiment of the invention.

FIG. 8 is a schematic diagram showing an example arrangement of thin film electronics 74 in the array element circuit 84. The array element circuit 84 may contain an actuation circuit 46, having inputs ENABLE, DATA and ACTUATE and an output which is connected to an element electrode 38. The array element circuit may further contain a sensor circuit 48. The sensor circuit 48 has an input which is connected to an element electrode, one or more row addressing lines RW and an output which is connected to an output line OUT. Optionally certain circuit components (e.g. transistors, capacitors) or addressing lines may perform functions associated with the operation of both the actuation circuit 46 and the sensor circuit 48, and these circuit components may be considered to comprise a part of both the actuation circuit and sensor circuit.

Figure 9:
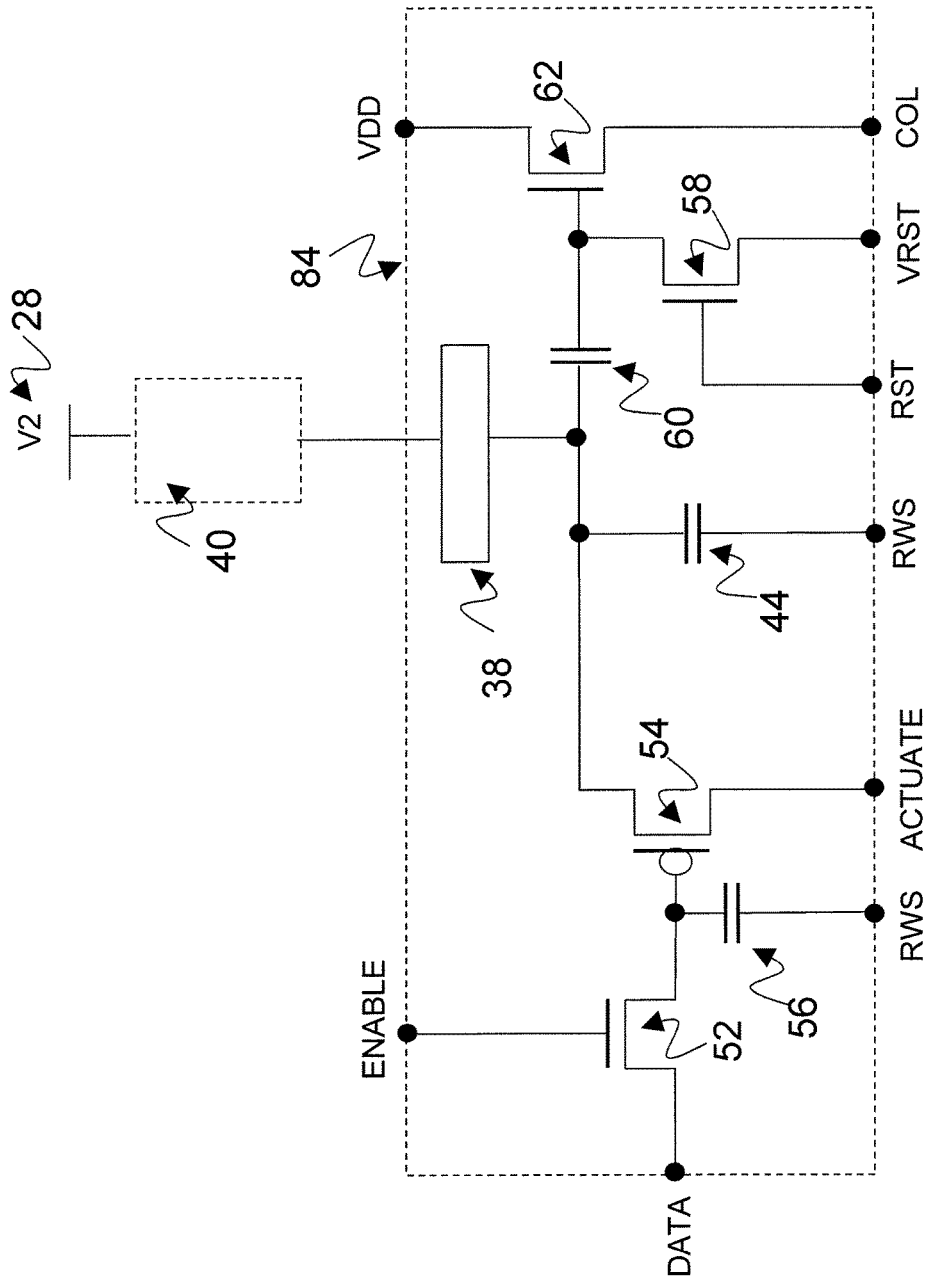
FIG. 9 is a schematic diagram depicting the array element circuit for use in the array elements of the exemplary AM-EWOD device of FIG. 4 according to a first embodiment of the invention.

FIG. 9 shows an array element circuit 84 according to a first embodiment of the invention. The array element circuit comprises n-type transistors 52, 58 and 62, a p-type transistor 54 and capacitors 56, 44 and 60. The element electrode 38, the load present at the element electrode 40 and the reference electrode 28 are shown since they play a role in the operation of the array element circuit 84. The reference electrode may thus be considered to form a part of the array element circuit in the description that follows.

The array element circuit 84 may typically perform the functions of:
  (i) Programming data to a memory element contained within the actuator circuit and storing said data. The data to be programmed is typically input by means of an addressing line DATA which may be common to all elements within the same column of the array. The programming of data may typically be controlled by an addressing line ENABLE, which may typically be common to all elements within the same row of the array.
  (ii) Supplying a voltage signal to the array element electrode 38, for example as supplied by an input signal V1 which is supplied to input ACTUATE, or alternatively switching the element electrode 38 in to a high impedance state.

The array element circuit according to this embodiment and shown in FIG. 9 is connected as follows. The drain of transistor 52 is connected to the input DATA which may be common to all elements in the same column of the array. The gate of transistor 52 is connected to the input ENABLE which may be common to all elements in the same row of the array. The source of transistor 52 is connected to the gate of transistor 54. Capacitor 56, referred to more specifically as a memory capacitor, is connected between the gate of transistor 54 and an addressing line RWS which may be common to all elements in the same row of the array. The drain of transistor 54 is connected to input signal ACTUATE which may be common to all elements in the array. Capacitor 44, referred to more specifically as the reference capacitor, is connected between the element electrode 38 and addressing line RWS. Capacitor 60, referred to more specifically as the sensor capacitor, is connected between the element electrode 38 and the gate of sensing transistor 62. The drain of sensing transistor 62 is connected to a DC voltage source VDD, which may be common to all elements in the array. The source of sensing transistor 62 is connected to output COL which may be common to all elements in the same column of the array. Transistor 58 is connected between the gate of sensing transistor 62 and a voltage supply VRST which may be common to all elements in the array. The gate of transistor 58 is connected to an input signal RST which may be common to all elements in the same row of the array. The actuator circuit 46 comprises transistor 52, transistor 54 and memory capacitor 56 and the terminal connections DATA, ENABLE and ACTUATE. The sensor circuit comprises memory capacitor 56, reference capacitor 44, sensor capacitor 60, transistor 54, transistor 58, transistor 60, addressing lines RST, VRST and output line COL. Transistor 54, capacitor 56, the element electrode 38, the electrode load 40, the reference electrode 28 and addressing line RWS form a part of both the actuator circuit and sensor circuit.

The operation of the array element circuit 84 is described as follows. The array element circuit performs two functions including (1) actuation and (2) impedance sensing.

(1) Actuation

The actuation circuit has two parts, a memory part and an actuation part. Generally, the memory part is configured for storing data, which may be digital data, corresponding to either an actuated state or an unactuated state of the array element, and the actuation part is configured for supplying the actuation voltages to the element electrode and the reference electrode.

The memory part is explained as follows. The memory part includes two transistors 52 and 54 for controlling the storing of the voltage data on the memory capacitor. Transistor 52 and memory capacitor 56 between them function as a Dynamic RAM (DRAM) memory element, capable of programming and storing data within the array element circuit 84. To program data, a voltage is programmed onto the column addressing line DATA. The ENABLE line is then taken high to switch transistor 52 on. The voltage on DATA is then programmed onto capacitor 56 and is held there once ENABLE is taken low, irrespective of how the voltage on input line DATA may subsequently be varied after ENABLE is taken low. In typical operation, the programmed voltage may be digital and be approximately $0.5 \times V_{EW}$ (for programming a "0" state, the droplet being unactuated in this state) or $-0.5 \times V_{EW}$ Volts (for programming a "1" state, the droplet being actuated in this state).

Figure 10:
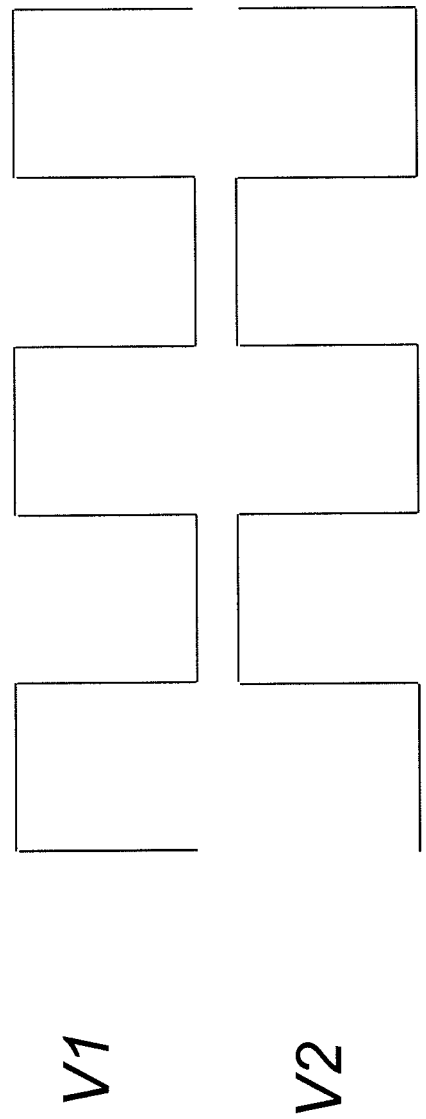
FIG. 10 is a timing diagram showing the timings of voltage pulses V1 and V2 according to a first embodiment of the invention.

The actuation part is explained as follows. An AC voltage signal V1 is applied to input ACTUATE and an AC voltage signal V2 is applied to the reference electrode 28. V1 and V2 are arranged to be in anti-phase (e.g. 180 degrees out of phase), or substantially in antiphase (e.g. a high phase angle out of phase for example greater than 90 degreed out of phase, or greater than 135 degrees out of phase or greater than 160 degrees out of phase). An example arrangement of voltage signals V1 and V2 is shown in FIG. 10. Each of V1 and V2 are switched between a low level of $-0.5 \times V_{EW}$ Volts and a high level of $0.5 \times V_{EW}$, V1 is high when V2 is low and vice versa. The element electrode 38 is actuated when a "1" is programmed to the memory (a voltage of $-0.5 \times V_{EW}$ programmed to the gate of transistor 54). In this case transistor 54 is turned on and so voltage signal V1 is transmitted to the element electrode 38. The voltage developed across the electrical load 40 (the electro-wetting voltage) is therefore V1−V2 which is an AC voltage waveform that varies in time between $-V_{EW}$ and $+V_{EW}$.

The element electrode 38 is non-actuated when a "0" is programmed to the memory (a voltage of $0.5 \times V_{EW}$ programmed to the gate of transistor 54). In this case transistor 54 is turned off. The element electrode 38 therefore exists in a high impedance state. There are two different cases where (1) a droplet is present at the element electrode 38 (the electrical load 40A is as FIG. 6A) and (2) no droplet is present at the element electrode 38 (the electrical load 40B is as FIG. 6B).

Case 1—Droplet Present:

Where a droplet is present, the dominant electrical coupling of the element electrode 38 is to the reference electrode 28 via the electrical load 40. As previously explained, the electrical load in this case 40A may be approximated by a capacitor whose value is typically of order a pico-Farad. The capacitance of the electrical load 40A will then dominate over other parasitic impedances in the circuit (e.g. that associated with the source-gate capacitance of transistor 54, typically of order femto-Farads). The electrical potential of the element electrode 38 will therefore track the potential of the reference electrode 28, and will thus correspond to a good approximation to the voltage signal V2. This being the case, the potential developed between the element electrode 38 and the reference electrode 28 will approximately be zero. The liquid droplet 4 will therefore be in a non-actuated state, the contact of the liquid droplet 4 with the hydrophobic coating 16 will not be energized and the liquid droplet 4 will not experience an electro-wetting force.

Case 2—No Droplet Present:

When no liquid droplet 4 is present, the capacitance between the element electrode 38 and the reference electrode 28 is very small as previously explained. The element electrode 38 is therefore now in a high impedance state and its effective potential is only poorly defined, being dependent on the multiple small parasitic capacitances and resistances within the circuit (e.g. the small electrical load 40B capacitance to the reference electrode 28, the small parasitic source to gate capacitance of transistor 54, and the large off resistance of transistor 54). It may therefore be unclear what the effective potential of the element electrode 38 is and therefore the extent to which the element electrode 38 remains effectively non-actuated.

However, the situation is such that, even with the potential of the element electrode 38 being poorly defined in Case 2, the device can still support the correct transport of liquid droplets 4. This is because if any liquid droplet does encroach into the position of the non-actuated element electrode 38, there is associated with this a significant increase in the capacitance between the reference electrode 28 and element electrode 38B. In this situation, the potential of the element electrode 38B becomes approximately that of the reference electrode 28 by means of the capacitive coupling through the liquid droplet 4. In other words the situation begins to resemble more closely Case 1 than Case 2, and the element electrode is in a non-actuated state. This effect is explained in further detail in co-pending application UK Application GB1500261.1.

An advantage of the array element actuation circuit and method of driving described in this embodiment is that the electro-wetting voltage in the actuated state is switched between $+V_{EW}$ and $-V_{EW}$. Therefore, AC electro-wetting is implemented. This is achieved whilst only requiring the array element circuit 84 to switch approximately $V_{EW}$ between the terminals of any transistor in the circuit (for the reasons why this may only be approximate see the more detailed description in UK Application GB1500261.1). This is an important advantage of the invention, since typically electro-wetting requires relatively high voltages to actuate the liquid droplets, whilst typical electronics technologies for realizing the thin film electronics 74 impose limitations on the maximum voltage applied to the transistors (e.g. due to reliability concerns).

A further advantage of this embodiment is that the actuation part of the array element circuit 84 has been implemented with only two transistors and one capacitor. Smaller array elements/element electrodes may therefore be realized. Smaller array elements may be advantageous for at least three reasons. Firstly, smaller liquid droplets may be manipulated. Secondly, if using larger liquid droplets, sub-droplet resolution of actuation may be achieved. Thirdly, smaller array element sizes facilitate the design and fabrication of a very large format array which may have a total number of array elements in excess of 1 million and which may be able to manipulate tens to hundreds of thousands of droplets simultaneously and independently. These advantages are described in more detail in UK Application GB1500261.1, incorporated by reference.

(2) Impedance Sensor

The operation of the impedance sensor function is based on the principles of U.S. Pat. No. 8,547,111 (Hadwen, issued Oct. 1, 2013) and U.S. Pat. No. 8,653,832 (referenced in the background section), incorporated by reference.

Figure 11:
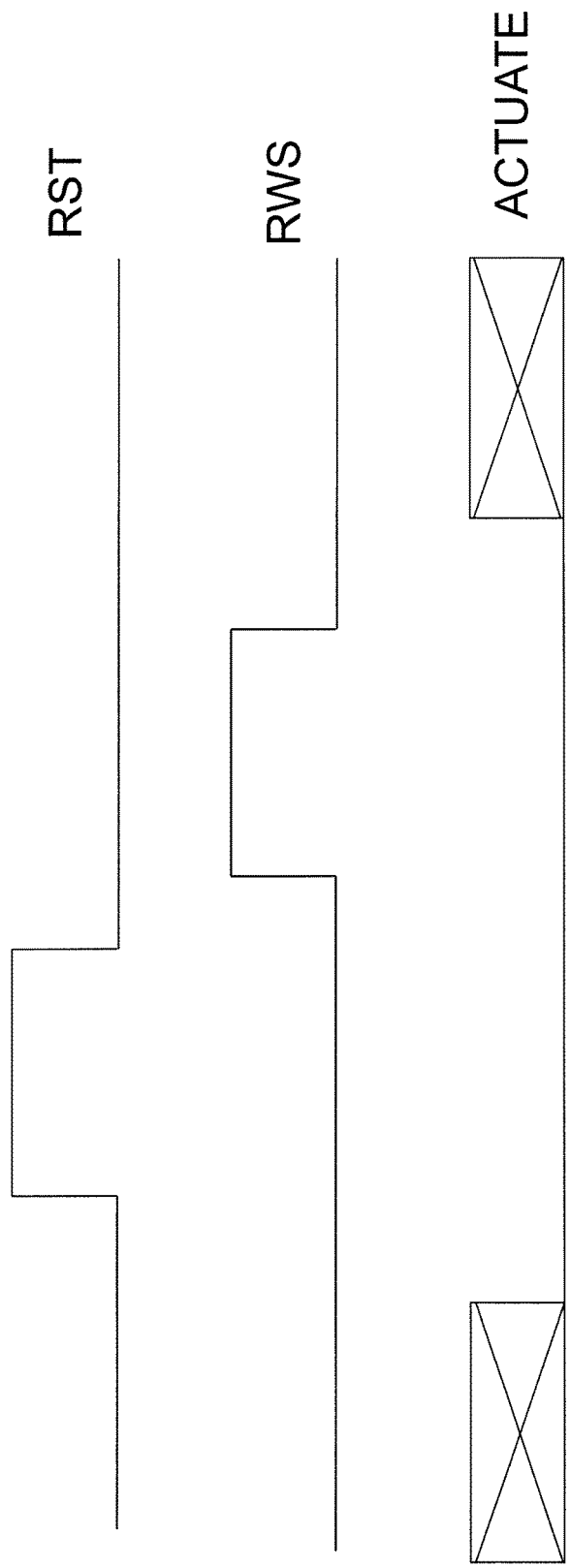
FIG. 11 is a timing diagram showing an exemplary arrangement of the timing signals for driving the array elements of the exemplary AM-EWOD device of FIG. 4 according to a first embodiment of the invention.

The circuit works in essence by comparing the impedance of the reference capacitor, capacitor 44, with the electrical load 40 presented at the element electrode 38. The operation of the impedance sensor function is explained with reference to the exemplary timing diagram shown in FIG. 11, showing the timings of the addressing signals RST, RWS and ACTUATE during the sensor operation as follows:

The ACTUATE signal is first taken to a low level.

The reset signal RST is taken high for a period of time which may be denoted the reset period. During the reset period transistor 58 is turned on and the gate of sensing transistor 62 is charged to the reset potential VRST. Typically the value of VRST may be chosen such that sensing transistor 62 is turned off. Following the conclusion of the reset period, RST is taken low so that transistor 58 remains turned off. The potential at the gate of transistor 62 remains at substantially VRST with this node now in a high impedance state.

A row select line that provides a row select signal input RWS is now taken high. This has two effects on the circuit as follows:

1) The row select line provides an input to the memory capacitor 56, and the input from the row select line to the memory capacitor 56 operates to isolate the array element from the actuation voltage during the operation of the impedance sensor circuit. Taking RWS high causes a perturbation in the potential at the gate of transistor 54. Charge is injected across capacitor 56 with the result that the potential at the gate of transistor 54 is increased. The magnitude of the RWS pulse amplitude (ΔVRWS) may be chosen such that perturbation in the potential of the gate of transistor 54 is sufficiently large such that in the case where a "0" is programmed to the memory of the array element (such that prior to the perturbation transistor 54 was turned on), the perturbation results in transistor 54 now being turned off for the duration of the RWS pulse. The effect of the RWS pulse on this part of the circuit is therefore to ensure that transistor 54 is turned off. It therefore isolates the ACTUATE signal from the element electrode for the duration of the RWS pulse, thus facilitating the sensing operation.

2) The impedance sensor circuit operates by forming a potential divider between the reference capacitor and the reference capacitor 44. Specifically, the row select signal, RWS, is also connected to one of the terminals of reference capacitor 44. A further result of the row select signal is the injection of charge across capacitor 44 thus perturbing the potential at the element electrode 38. Capacitor 44, whose value may be represented by $C_S$, forms a potential divider with the load circuit 40 and the sensor capacitor 60, the latter whose value may be represented as $C_C$. Therefore, in the case where a liquid droplet 4 is presented at the element electrode 38, the perturbation of the potential at the element electrode is approximately given by:

$$\Delta V_A = V_0 + \Delta VRWS \frac{C_S}{C_S + C_I + C_C} \quad \text{[equation 1a]}$$

Where $V_0$ is the initial potential at the element electrode and $C_I$ is as previously defined.

In the case where no liquid droplet 4 is present at the element electrode 38 the perturbation at the element electrode is given by:

$$\Delta V_A = V_0 + \Delta VRWS \frac{C_S}{C_S + C_{OIL} + C_C} \quad \text{[equation 1b]}$$

Where $C_{OIL}$ is as previously defined.

The perturbation of the potential at the element electrode further causes an injection of charge across the sensor capacitor 60. The potential at the gate of sensing transistor 62 therefore becomes:

$$\Delta V_B = VRST + \Delta V_A \frac{C_C}{C_{par} + C_C} \quad \text{[equation 2]}$$

Where $C_{par}$ represents the parasitic capacitances at the gate of sensing transistor 62 and associated with transistors 58 and 62.

The overall function of the RWS pulse input from the row select line to the reference capacitor 40 is therefore twofold:

(1) To electrically isolate the element electrode from the input line ACTUATE by turning off transistor 54 (in the case where it was not turned off already).

(2) To perturb the potential at the gate of sensing transistor 62 by an amount that depends on the impedance of the load circuit 40. In the case where a droplet is present at the element electrode 38, the perturbation ($\Delta V_B$) is small and sensing transistor 62 may remain turned off, or only slightly turned on for the duration of the RWS pulse, and a small current is sourced through the output COL. In the case where no droplet is present at the element electrode 38, the perturbation ($\Delta V_B$) is large and sensing transistor 62 is turned on so that a large current is sourced through the output COL. The current through the output COL may typically be measured by means of standard circuitry in the column detection circuit 86. This may be done using standard techniques for CMOS image sensor as is very well known.

It will be noted from the description above that an important feature of the circuit is that the gate of sensing transistor 62 is AC coupled to the element electrode. An advantage of this arrangement is that the potential at the gate of sensing transistor 62 $V_B$ (as produced by the perturbing effect of the RWS pulse and the subsequent potential dividing) is independent of the initial voltage $V_0$ of the element electrode 38. A further advantage is that the total range of voltage that may be produced at the gate of sensing transistor 62 may be much smaller than the range of voltages that may be produced at the element electrode 38. Therefore transistors 62 and 58 may be formed from a standard low voltage device construction (e.g. 5 Volt or 8 Volt transistors).

Figure 3:
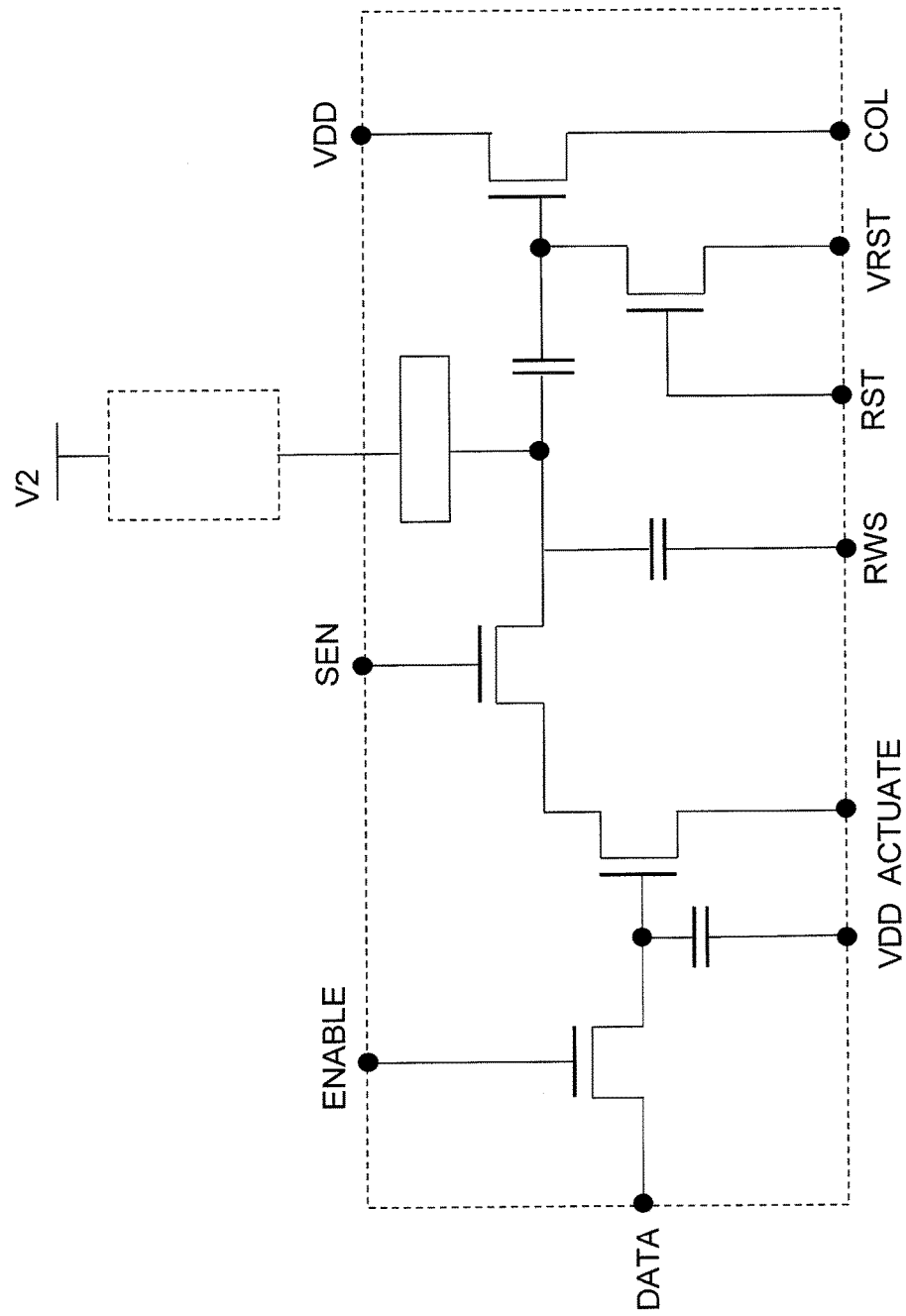
FIG. 3 shows prior art, particularly a 2-transistor AM-EWOD array element actuation circuit with additional impedance sensor function.

It will be appreciated in the above description that a critical part of the sensor operation is that transistor 54 is turned off, thus isolating the element electrode from the signal ACTUATE for the duration of the RWS pulse. If this was not the case, the potential of the element electrode would remain substantially pinned to the potential of ACTUATE and the potential divider would not work as described. Accordingly, the inventors have realized that the disconnection of the actuate signal from the element electrode may be achieved without recourse to an additional isolation transistor (for example as shown in the prior art circuit FIG. 3 disclosed in UK Application GB1500261.1. In this prior art the disconnecting of the voltage signal applied to ACTUATE from the element electrode 38 is implemented by means of an additional switch transistor and an additional addressing signal SEN (connected to the gate of said additional transistor).

However, in the array element circuit of this embodiment of the present invention, transistor 54 is arranged to fulfill an additional function (compared to the prior art circuit of FIG. 3) in effecting the isolation of ACTUATE from the element electrode 38 during the sense operation. Transistor 54 fulfills this role in addition to its function as an access transistor during the actuate operation. Transistor 54 thus performs a dual function and plays a role in both the actuate and sense operations. Furthermore, the array element circuit of this embodiment also does not require an additional addressing line (for example as addressing line SEN in the prior art circuit of FIG. 3). The addressing line RWS is configured to perform the dual operations of both turning off transistor 54 and providing an interrogation signal to the potential divider part of the circuit.

A significant advantage of this embodiment is that the array element circuit 84, having both an actuate and sensor function, has been implemented with a minimal number of circuit components and addressing lines. For example, the array element circuit has one fewer transistor and one fewer addressing line than the array element circuit in prior art of UK Application GB1500261.1 and as reproduced in FIG. 3.

Reducing the complexity and the number of transistors in the array element circuit 84 is advantageous for several reasons:

Smaller array elements/element electrodes may be realized. Typically it is often the case that the minimum achievable array element size is set by the limitations of the thin film electronics and the design for fabrication requirements (design rules) dictating the layout of the array element circuit 84 in thin film electronics. A simpler circuit (fewer transistors) therefore enables smaller array elements to be designed and fabricated. Smaller array elements may be advantageous for at least three reasons. Firstly, smaller liquid droplets may be manipulated. This is particularly important for applications involving the manipulation or analysis of single cells or single molecules. Secondly, if using larger liquid droplets, sub-droplet resolution of actuation may be achieved. This may improve the capabilities of the device, for example enabling more accurate splitting or faster mixing. Thirdly, smaller array element sizes facilitate the design and fabrication of a very large format array which may have a total number of array elements in excess of 1 million and which may be able to manipulate tens to hundreds of thousands of droplets simultaneously and independently.

A smaller and simpler design of array element circuit 84 may facilitate increased manufacturing yield and hence lower cost of the device.

A smaller and simpler design of array element circuit 84 may facilitate increased optical transparency of the device. This may be important, for example, if the device is being used to implement chemical or biochemical tests that result in a change in the optical properties (e.g. fluorescence, absorbance) of one or more liquid droplets and that by measurement of this change in optical property the device may be read out.

A smaller and simpler design of array element circuit 84 may free up space within the array element to implement other electronic functions into the array element, e.g. temperature sensing, bio-sensing and like operations.

Typically, but not necessarily, on the rows of the sensor not being sensed, RST is maintained high such that the potential at the gate of sensing transistor 62 is pinned to VRST so that sensing transistor 62 is maintained switched off for all elements in the rows not being sensed.

Optionally, the signal ACTUATE may be common only to elements in the same row of the array. If this is the case it is not necessary to maintain ACTUATE at a low level for the rows of the array not being sensed, providing that perturbations of the potential at the gate of sensing transistor 62 are not sufficiently large to turn sensing transistor 62 on or partially on in any of the rows of the array not being sensed. This condition may be achieved by maintaining RST high on the rows not being sensed for the duration of the sensing operation. Making the ACTUATE signal common only to elements in the same row of the array has the advantage that it is not necessary to interrupt the actuation operation on the rows of the array not being sensed.

Alternatively, making the ACTUATE signal common to all elements in the array has the advantages that in the layout of the circuit a single physical line may supply the signal to two rows of the array, thus minimizing the area required and the reducing the minimum size of array element that may be realized within the design rules of the manufacturing process.

According to a further variant, it is also possible to re-start the ACTUATE signal following the rising edge of the RWS pulse on all rows of the array. For the rows of the array not being sensed, this will result in the ACTUATE signal coupling to the element electrode, or not, according whether a "1" or a "0" has been programmed to the array element. For the row being sensed, however, the perturbation at the gate of transistor 54 ensures that for elements in the row being sensed the transistor 54 always remains turned off. Therefore, for this row of the array the ACTUATE signal has no effect and the sensing operation can function as described.

Figure 12:
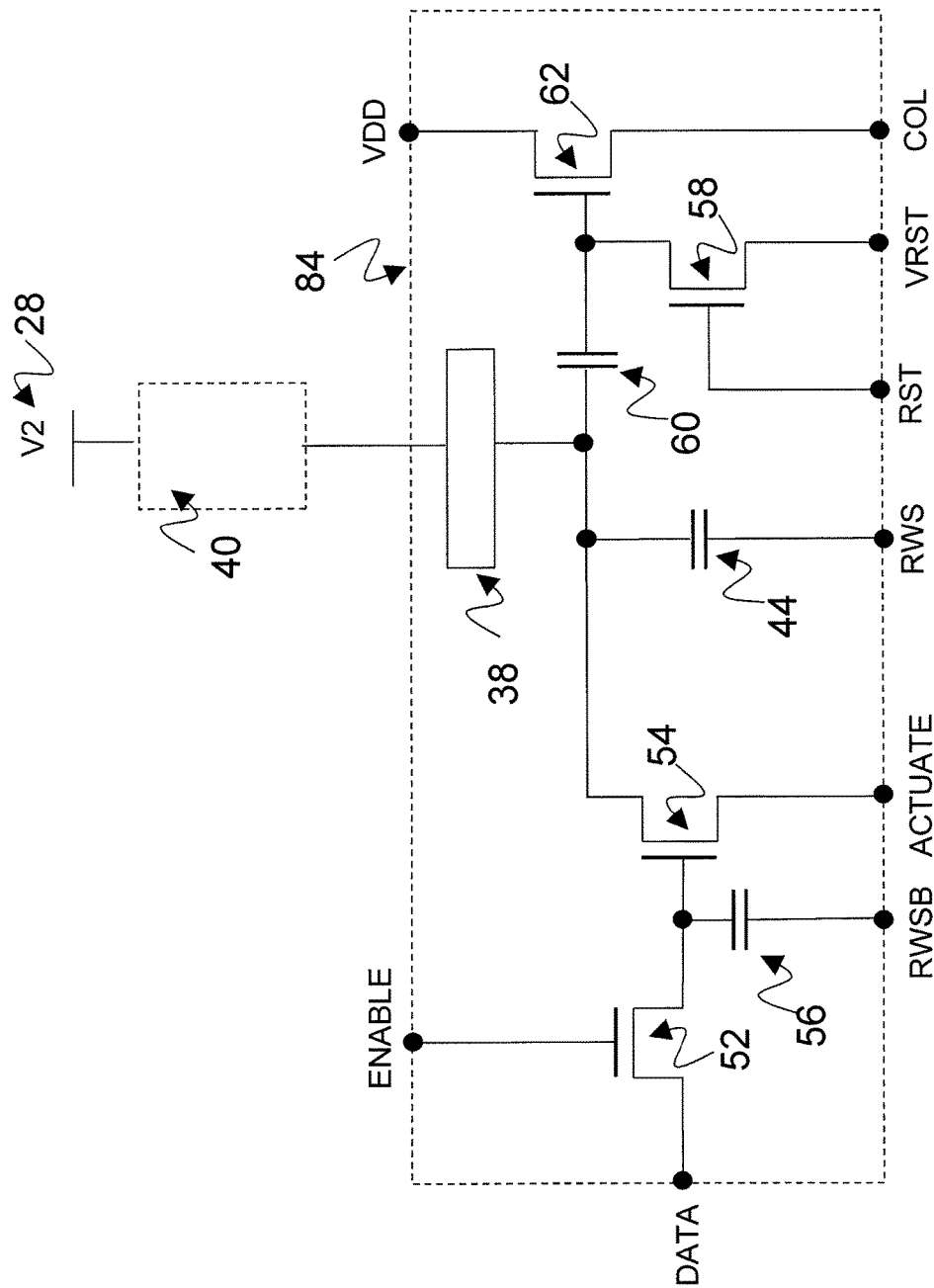
FIG. 12 is a schematic diagram depicting the array element circuit for use in the array elements of the exemplary AM-EWOD device of FIG. 4 according to a second and exemplary embodiment of the invention.

An AM-EWOD device according to a second embodiment of the invention is comparable to the first embodiment except that an alternative design of array element circuit is employed as shown in FIG. 12. The topology of the array element circuit is as the first embodiment with the exception that transistor 54 is an n-type device and the gate of transistor 54 is connected to another row select line that provides a row addressing signal input RWSB which may be common to all elements in the same row of the array. The operation of the array element circuit according to this embodiment is comparable as described for the first embodiment with the following differences:

Since transistor 54 is n-type, it is turned on when the potential at its gate is high, and turned off when the potential at its gate is low. To program the memory for control of the actuation voltage, a high voltage is written to the gate of the transistor 54 to correspond to programming "1" and a low voltage is written to the gate of transistor 54 to correspond to programming a "0".

Figure 13:
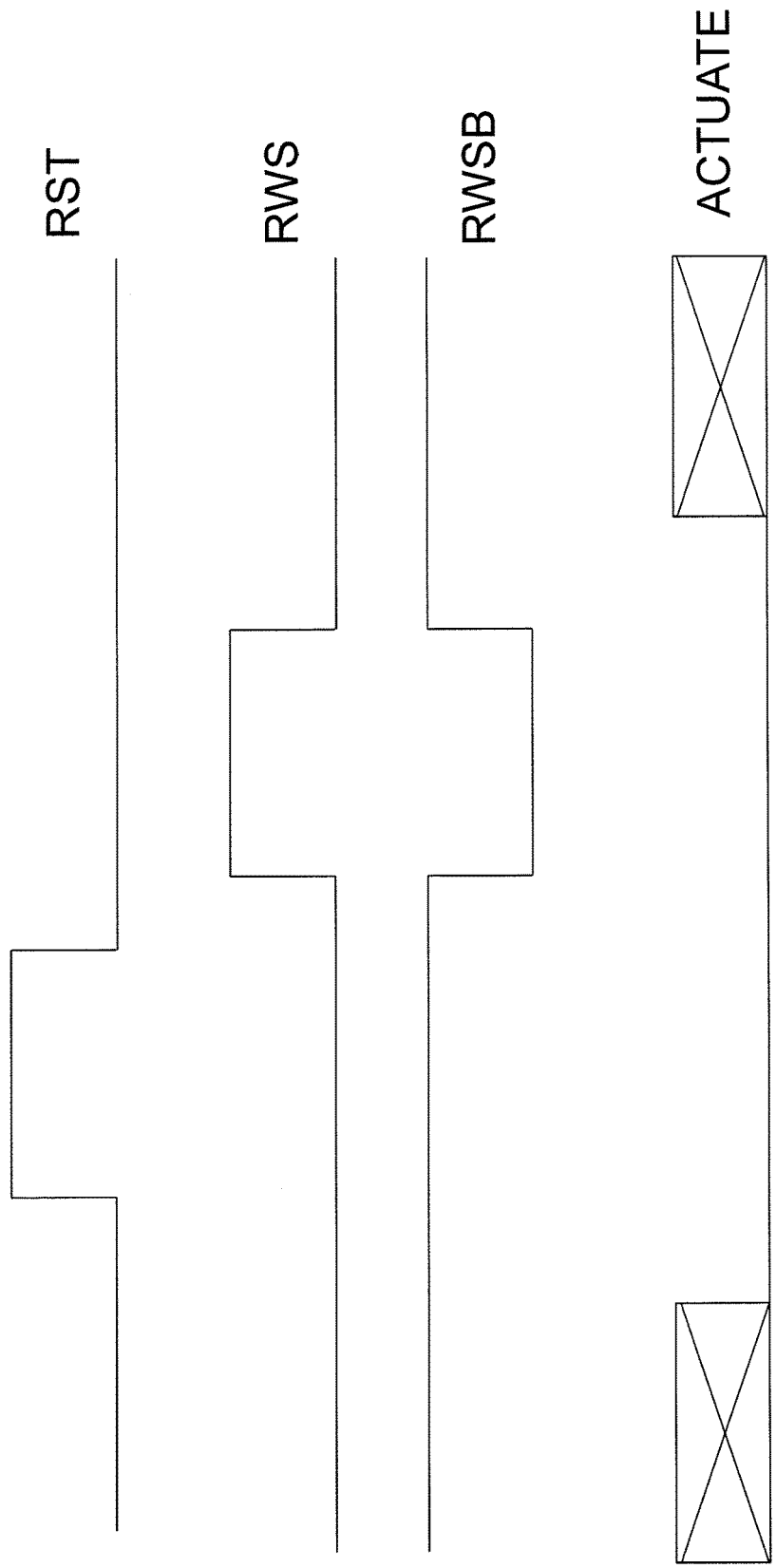
FIG. 13 is a timing diagram showing an exemplary arrangement of the timing signals for driving the array elements of the exemplary AM-EWOD device of FIG. 4 according to a second embodiment of the invention.

RWSB from the another row select line may constitute a row addressing signal that is the logical inverse input of the RWS signal provided by the first row select line. Therefore, the timing signals of the second embodiment may be as shown in FIG. 13. The effect of the RWSB signal is that on falling edge, charge is injected across memory capacitor 56 and the potential at the gate of transistor 54 also falls correspondingly. The voltage swing associated with the RWSB transition and the operating voltages of the circuit may be arranged such that the following the RWSB falling edge transistor 54 is guaranteed to be always turned off, regardless of whether a "1" or a "0" was written to the memory.

The array element circuit of the second embodiment thus operates in a very similar way to that previously described for the first embodiment. As before, transistor 54 has a dual function, as an access transistor during the actuation operation and as an isolation transistor during the sensing operation.

Compared to the first embodiment, the array element of the second embodiment has one additional row addressing line RWSB. However, the second embodiment has the additional advantage that it only requires n-type transistors to implement the array element circuit. This may therefore facilitate fabrication of the AM-EWOD device with a simpler and lower cost fabrication process. This embodiment may also therefore be particularly suitable for AM-EWOD devices fabricated using a single channel thin film transistor fabrication process, for example based on amorphous silicon TFTs or oxide TFTs (e.g. zinc oxide or indium-gallium-zinc-oxide TFTs).

Optionally, the timing of the falling edge of the voltage signal supplied to RWSB may be delayed slightly with respect to the timing of the RWS rising edge signal. This may be advantageous to ensure that transistor 54 is fully turned off before RWS transitions high and potential division occurs. Operating in this way may thus prevent a race condition between transistor 54 turning off and potential division taking place leading to improved performance and reduced noise on the sensor signal output.

Figure 14:
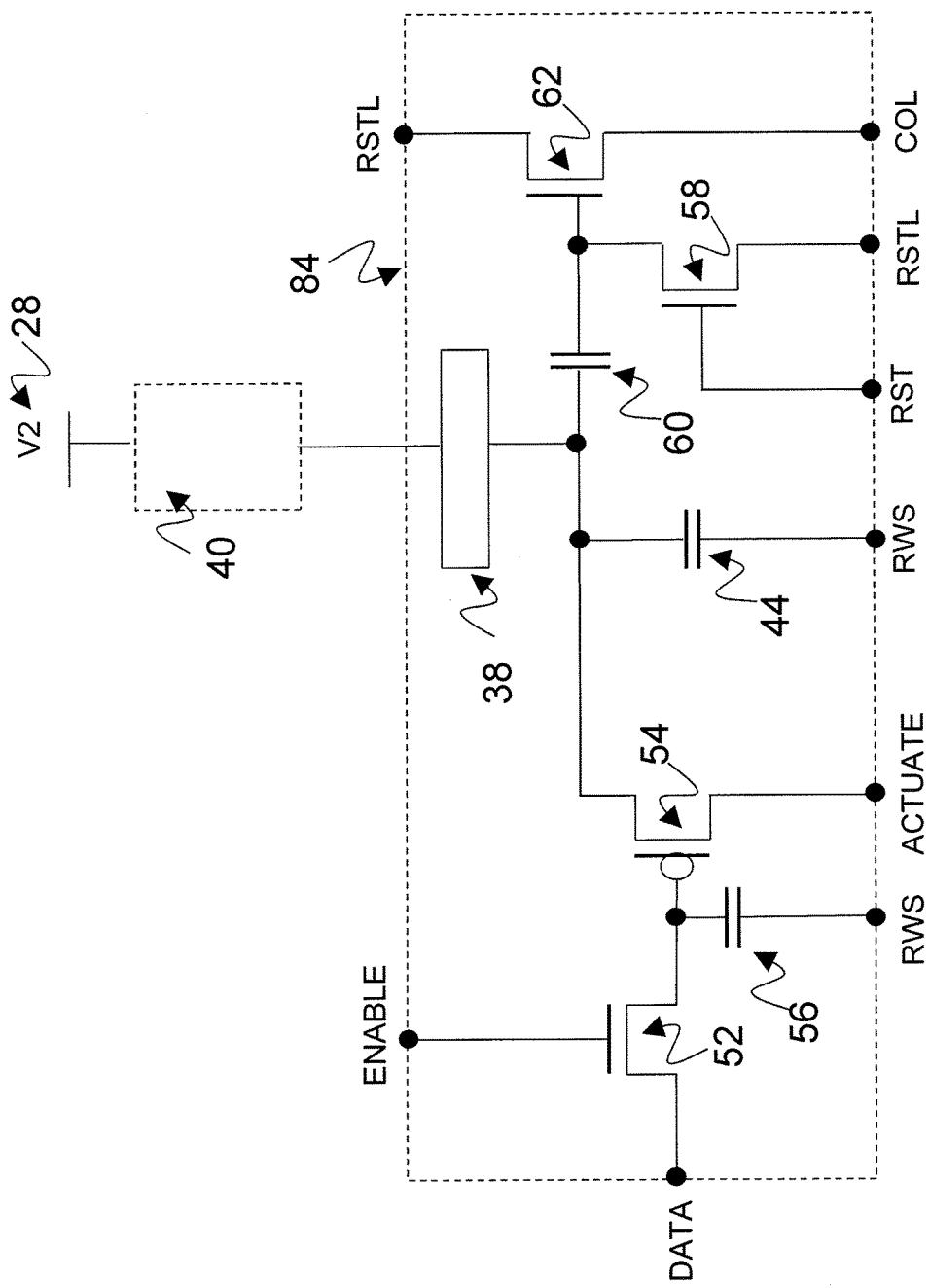
FIG. 14 is a schematic diagram depicting the array element circuit for use in the array elements of the exemplary AM-EWOD device of FIG. 4 according to a third and exemplary embodiment of the invention.

An AM-EWOD device according to a third embodiment of the invention is comparable the first embodiment with an alternative design of array element circuit as shown in FIG. 14. This array element circuit is comparable to the array element circuit of the first embodiment with the difference a common addressing line is connected to each of the two transistors 58 and 62 for setting the sensing voltage at the sensor capacitor. In particular, the drain of transistor 58 and the drain of sensing transistor 62 are connected to a common addressing line that provides input signal RSTL, which may be common to all elements in the same row of the array. The operation of the array element circuit according to this embodiment is similar to as previously described for the first embodiment, with the exception that the functions of the DC supply voltages VDD and VRST are combined into a single supply VRSTL which may be switched between the voltage levels VRST and VDD during the operation of the circuit.

This embodiment exploits the fact that both of the following DC potential levels of nodes within the circuit are unimportant for the operation of the sensor function:

The potential at the drain of sensing transistor 62 during the reset operation. This is because sensing transistor 62 remains switched off during the reset operation. The current through sensing transistor 62 is small and almost independent of the potential of the drain of sensing transistor 62 during the reset operation and has no influence on the overall operation of the circuit.

The potential at the drain of transistor 58 during the time when RWS is taken high. This is because the transistor 58 remains switched off once the reset operation is concluded. The potential at the drain of transistor 58 therefore has no influence on the potential at the gate of sensing transistor 62 once the reset operation is concluded.

Figure 15:
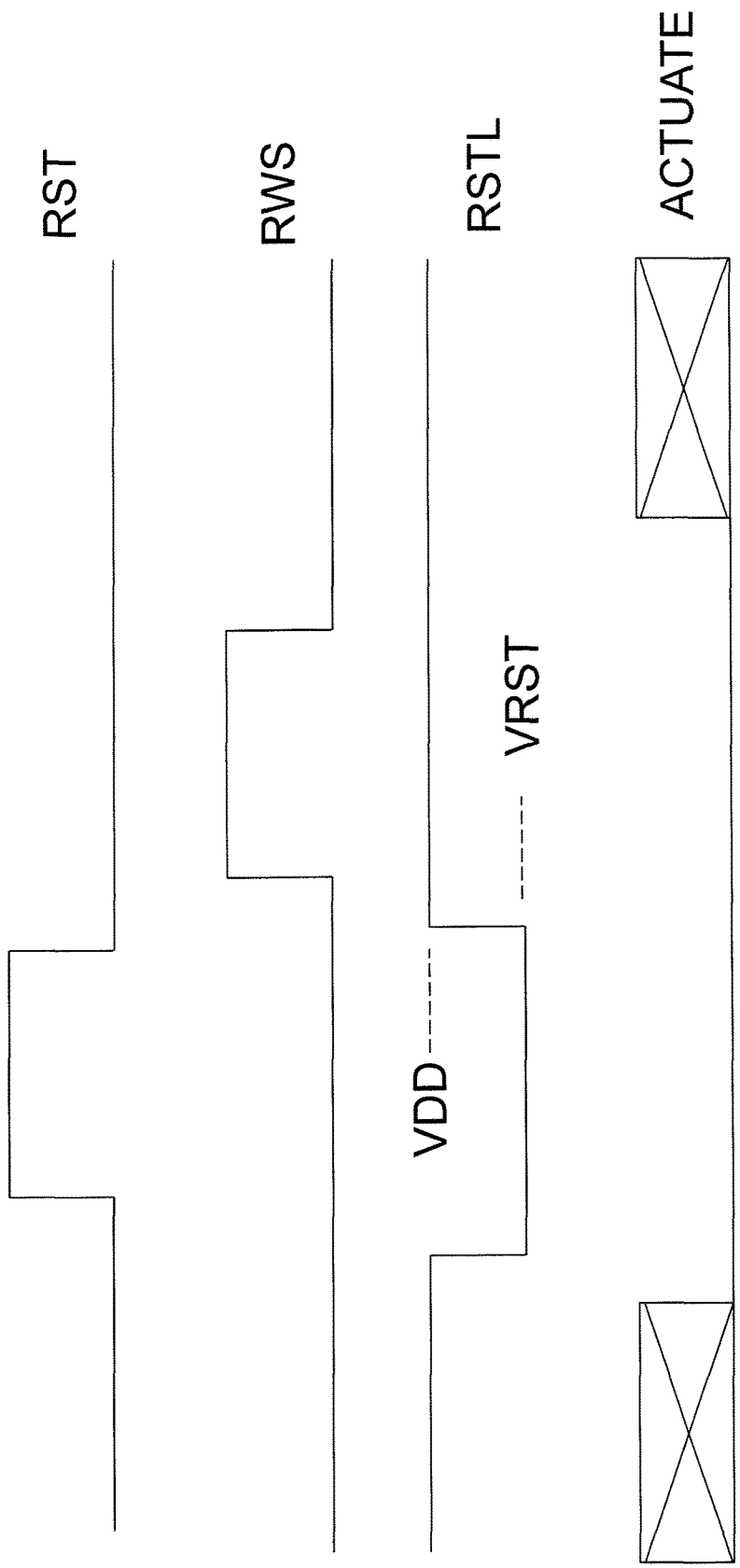
FIG. 15 is a timing diagram showing an exemplary arrangement of the timing signals for driving the array elements of the exemplary AM-EWOD device of FIG. 4 according to a third embodiment of the invention.

An example timing chart showing the operation of the sensor function of the array element circuit according to this embodiment is shown in FIG. 15. The addressing line RWSL is modulated between voltage levels VRST and VDD. Initially VRSTL may be at VDD, then VRSTL is taken to voltage level VRST shortly before the rising edge of RST. Following the conclusion of the reset period and the falling edge of RST, RSTL is taken back to voltage VDD in time for the rising edge of RWS. Otherwise the device and array element circuit functions comparably as previously described.

An advantage of this embodiment is that by combining the voltage supplies VDD and VRST into a single addressing line RSTL, the array element circuit requires one fewer addressing line than the first embodiment. It therefore may be made smaller, with all the advantages of a smaller circuit as previously described.

Figure 16:
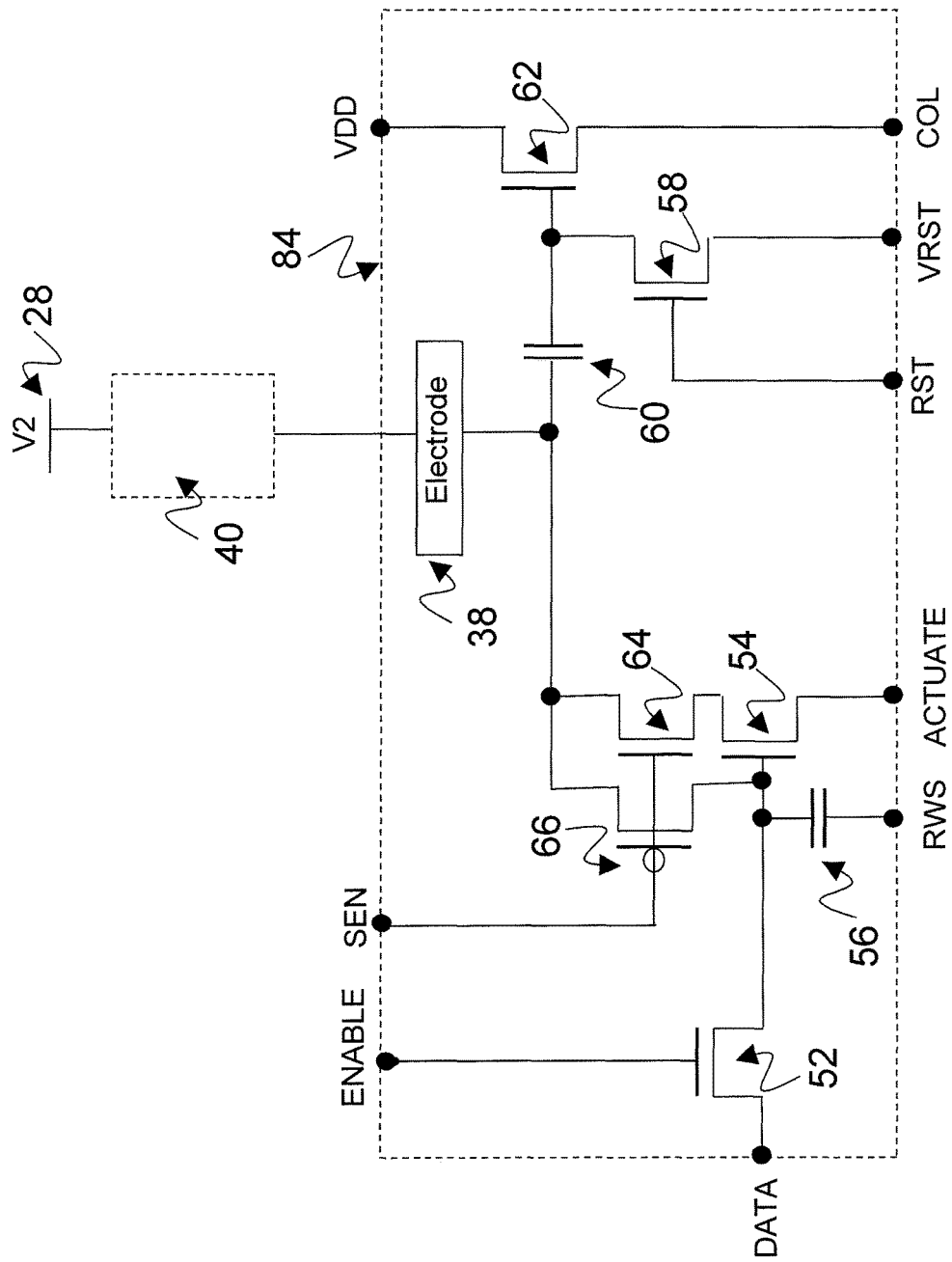
FIG. 16 is a schematic diagram depicting the array element circuit for use in the array elements of the exemplary AM-EWOD device of FIG. 4 according to a fourth and exemplary embodiment of the invention.

A fourth embodiment of the invention is comparable to the first embodiment with an alternative design of array element circuit as shown in FIG. 16.

The connectivity of the array element circuit is as follows:

The drain of transistor 52 is connected to the input DATA which may be common to all elements in the same column of the array. The gate of transistor 52 is connected to the input ENABLE which may be common to all elements in the same row of the array. The source of transistor 52 is connected to the gate of transistor 54. Capacitor 56 is connected between the gate of transistor 54 and an addressing line RWS which may be common to all elements in the same row of the array. The drain of transistor 54 is connected to input signal ACTUATE which may be common to all elements in the array. Transistor 64, which is n-type, is connected between the source of transistor 54 and the element electrode 38. Transistor 66, which is p-type is connected between the gate of transistor 54 and the element electrode 38. The gate of transistor 64 is connected to the gate of transistor 66 and sensor input addressing line SEN for actuating the impedance sensor circuit, which may be common to all elements in the same row of the array. Capacitor 60 is connected between the element electrode 38 and the gate of sensing transistor 62. The drain of sensing transistor 62 is connected to a DC voltage source VDD, which may be common to all elements in the array. The source of sensing transistor 62 is connected to output COL which may be common to all elements in the same column of the array. Transistor 58 is connected between the gate of sensing transistor 62 and a voltage supply VRST which may be common to all elements in the array. The gate of transistor 58 is connected to an input signal RST which may be common to all elements in the same row of the array. The actuator circuit 46 comprises of transistor 52, transistor 54, capacitor 56 and transistor 64 and the inputs DATA, ENABLE and ACTUATE. The sensor circuit comprises of capacitor 56, capacitor 60, transistor 66, transistor 58, transistor 62, and terminal connections RWS, RST, SEN, VRST and COL. Transistors 64 and 66, capacitor 56, the element electrode 38, the electrode load 40 and the reference electrode 28 form a part of both the actuator circuit and sensor circuit.

The operation of the array element circuit is described as follows:

(1) Actuation

The actuation function operation is similar to as previously described for the second embodiment of the invention. During actuation the addressing line SEN is at a high voltage level. Therefore transistor 64 is turned on and transistor 66 is turned off. In the case where a "1" is programmed to the array element, the gate of transistor 54 is at a high voltage level, transistor 54 is turned off and the input signal ACTUATE is connected through to the element electrode 38. In the case where a "0" is programmed to the array element, the gate of transistor 54 is at a low voltage level, transistor 54 is turned off and the element electrode is in a high impedance state. In other respects the ACTUATION operation functions as previously described.

(2) Impedance Sensor

Figure 17:
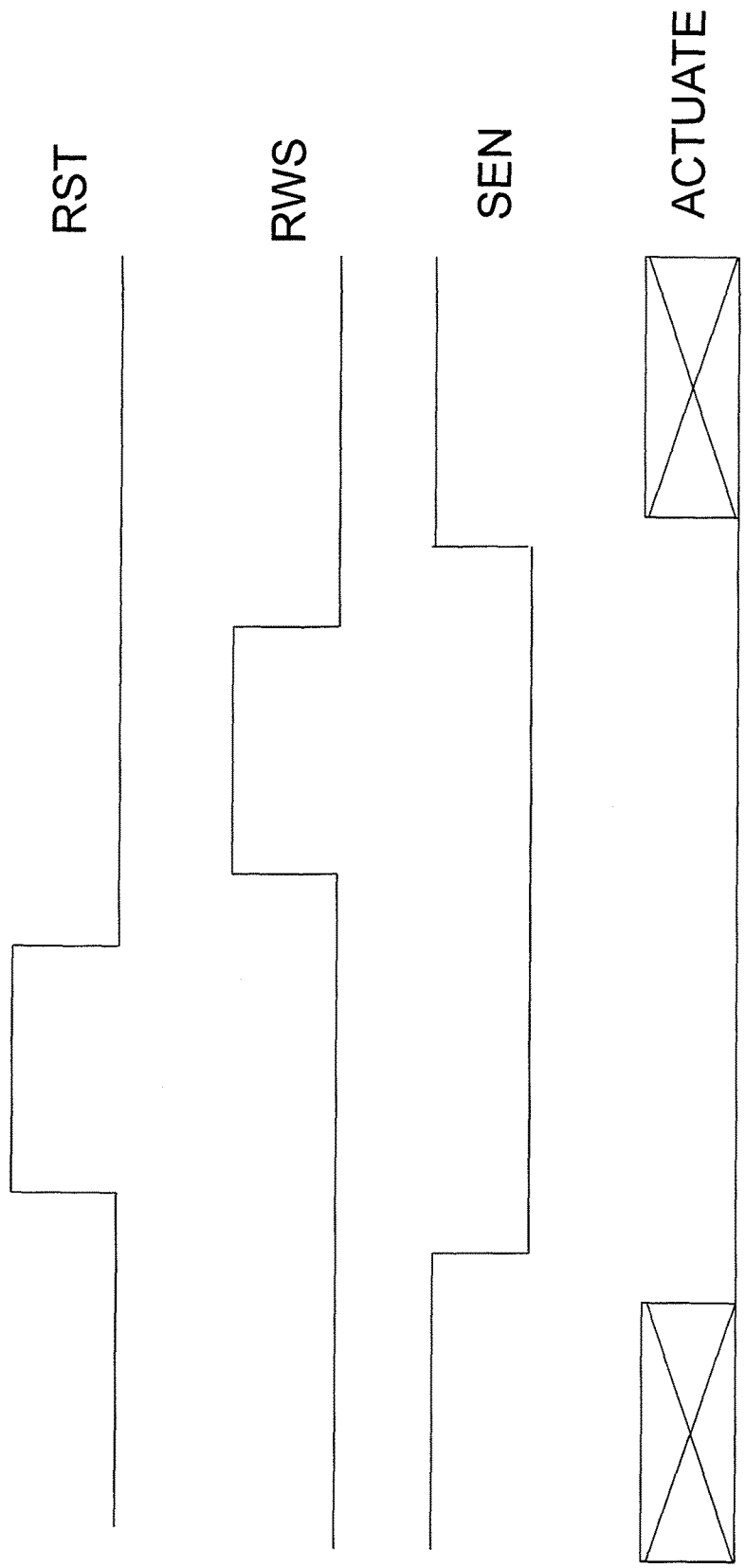
FIG. 17 is a timing diagram showing an exemplary arrangement of the timing signals for driving the array elements of the exemplary AM-EWOD device of FIG. 4 according to a fourth embodiment of the invention.

The impedance sensor functions in a similar manner as previously described, with the difference that memory capacitor 56 also functions as the reference capacitor to which the load impedance 40 is compared within the operation of the potential divider. The separate reference capacitor 44 of previous embodiments therefore is eliminated. The operation of the impedance sensor function of the array element circuit of FIG. 16 is described with reference to the timing diagram shown in FIG. 17.

At the beginning of the sensing operation, the input signal ACTUATE is taken to a low level. The input signal SEN is then taken to a low level. This has the effect of turning off transistor 64, and thus isolating the source of transistor 54 from the element electrode. Taking SEN to a low level also turns on transistor 66 so that the gate of transistor 54 becomes connected to the element electrode 38. The RST signal line is then taken high thus resetting the potential at the gate of sensing transistor 62 to the reset voltage level VRST as previously described. RST is then taken low again, followed by RWS being taken high. A potential divider is thus formed between memory capacitor 56, the load impedance 40 and sensor capacitor 60. The value of the voltage perturbation at the element electrode is described by equation 1a or 1b, as previously presented and explained, for the cases where a liquid droplet 4 is present or absent at the element electrode respectively, and where $C_S$ is the capacitance of capacitor 56. In other respects the operation of the impedance sensor is as previously described.

Alternatively and optionally, ACTUATE may be taken to a high level or may be alternated between a high and low level for the duration of the sensing operation. The operation of the impedance sensor function according to this embodiment of the invention utilizes memory capacitor 56 as part of both the actuate and the sensing operation. In the operation of the actuation function, capacitor 56 forms part of the memory function, acting in effect as the storage capacitor in a DRAM circuit. The array element is programmed by writing and storing a voltage, the programmed voltage being stored on capacitor 56, and controlling the potential at the gate of transistor 54. In the operation of the impedance sensor, one terminal of the capacitor 56 becomes connected to the element electrode (for the time for which transistor 66 is switched on) and the pulsing of the RWS addressing line injects charge across the capacitor 56 and onto the element electrode. Capacitor 56 thus functions as the reference capacitor to which the load impedance 40 is compared in the operation of the potential divider. Capacitor 56 therefore has a dual function, playing a role in the operation of both the actuate and impedance sensing operations.

An advantage of the fourth embodiment is that it removes the need for a capacitor connected directly between the element electrode 38 and the RWS addressing line (e.g. reference capacitor 44 as shown in FIG. 9). This capacitor, typically of value around 1 pF, is physically quite large and occupies a substantial portion of the total layout area of the element electrode circuit. The removal of this capacitor may therefore substantially reduce the physical size of the array element circuit, with all the advantages as previously described.

Variants of this embodiment combining features of previous embodiments are also possible. For example, a single channel circuit architecture (including only n-type transistors) could be realized by making transistor 66 of n-type construction and connecting the gate of transistor 66 to an additional row addressing line SENB which is driven by the logical inverse of the supply SEN.

A further variant is that the DC voltage supplies VRST and VDD may be combined, as for example described with respect to the third embodiment of the invention.

Figure 18:
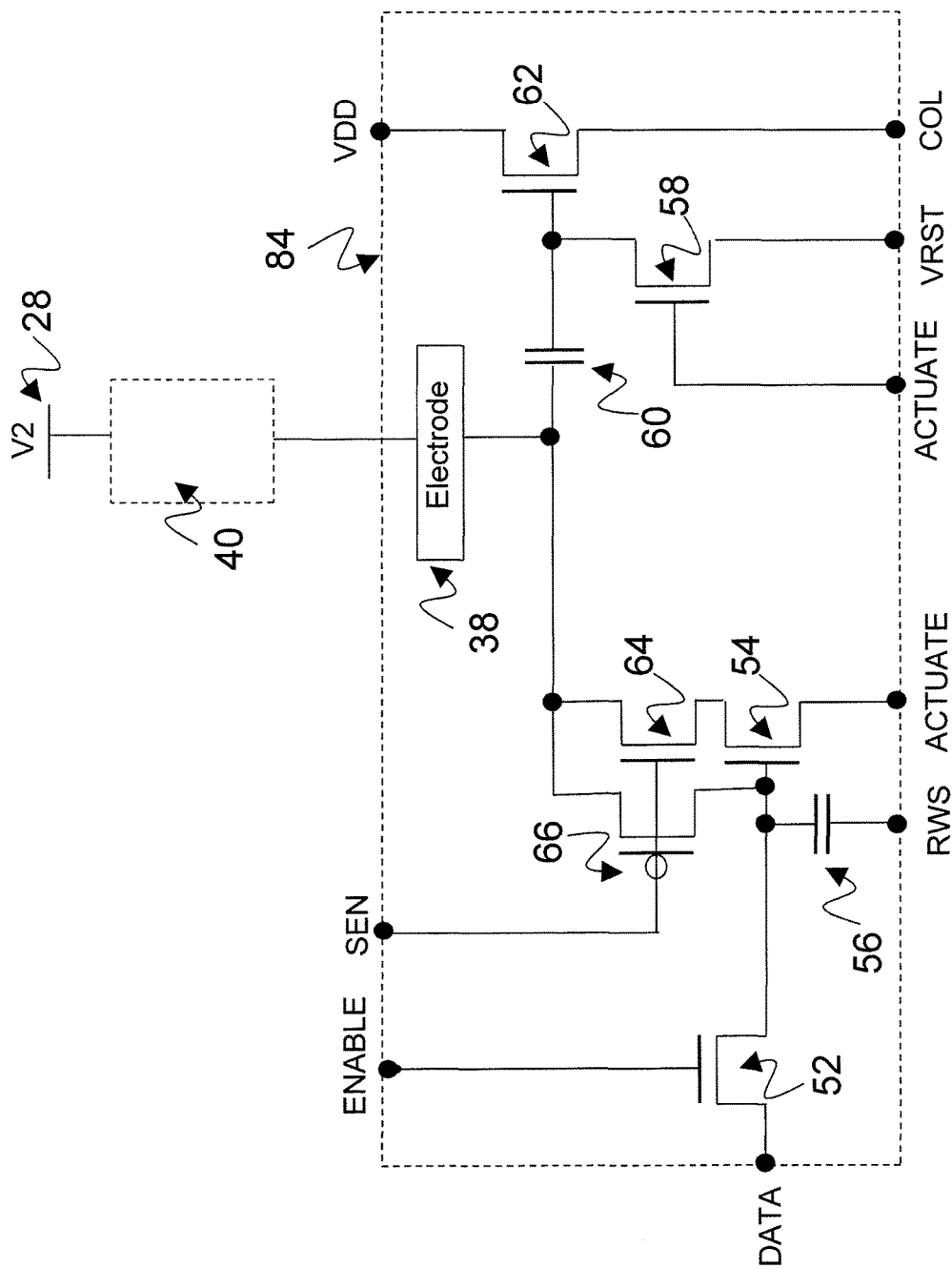
FIG. 18 is a schematic diagram depicting the array element circuit for use in the array elements of the exemplary AM-EWOD device of FIG. 4 according to a fifth and exemplary embodiment of the invention.
Figure 19:
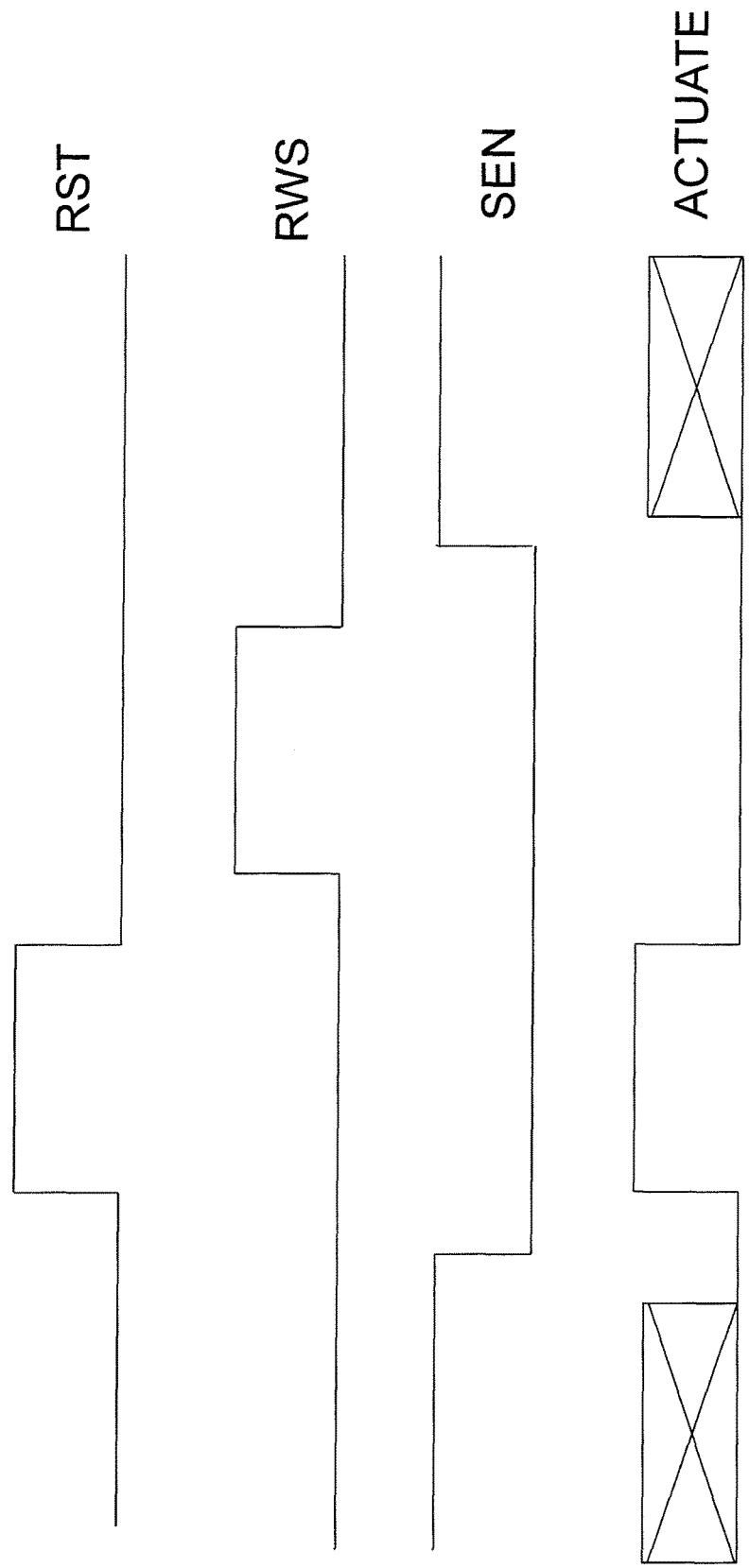
FIG. 19 is a timing diagram showing an exemplary arrangement of the timing signals for driving the array elements of the exemplary AM-EWOD device of FIG. 4 according to a fifth embodiment of the invention.

An AM-EWOD device according to a fifth embodiment of the invention is comparable to the fourth embodiment with a modified array element circuit as shown in FIG. 18. The array element circuit is modified from that of the fourth embodiment in that the gate of transistor 58 is connected to the voltage signal ACTUATE and the input signal RST is no longer required. According to the operation of this embodiment, the timings of the ACTUATE signal are varied to those shown in FIG. 19. According to this embodiment the signal ACTUATE performs the dual function of droplet actuation and the re-setting of the potential at the gate of sensing transistor 62.

An advantage of the fifth embodiment is that in comparison to the fourth embodiment one fewer addressing line is required. This affords the same advantages as previously described of reduced array element size.

Figure 20:
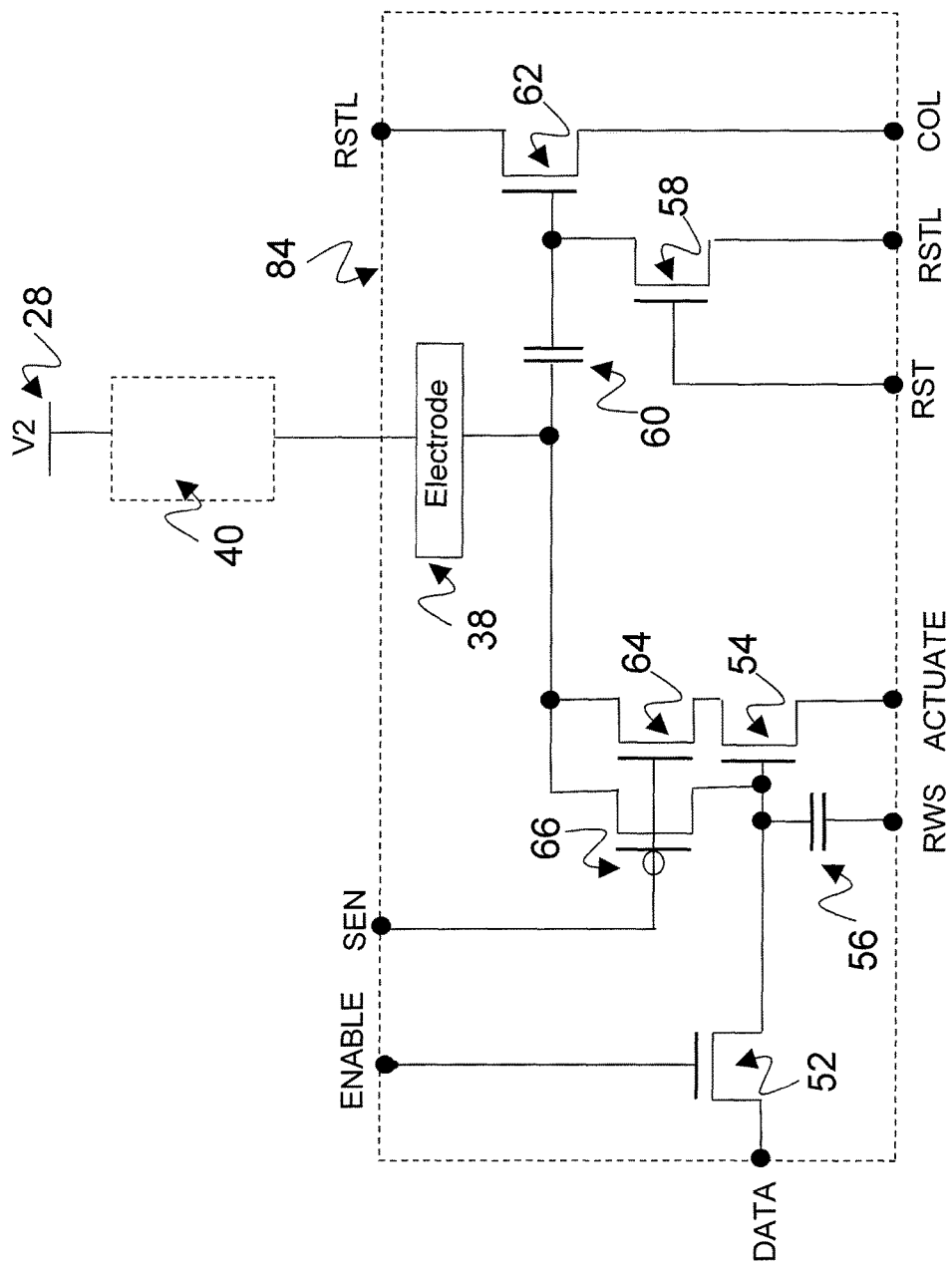
FIG. 20 is a schematic diagram depicting the array element circuit for use in the array elements of the exemplary AM-EWOD device of FIG. 4 according to a sixth and exemplary embodiment of the invention.

An AM-EWOD device according to a sixth embodiment of the invention has an array element circuit as shown in FIG. 20. This embodiment is comparable to the fourth embodiment but additionally incorporates the concept of the third embodiment of combining the DC voltage supplied VRST and VDD into a single supply line RSTL whose voltage may be modulated during the operation of the sense function. The timing diagram for the operation of the array element circuit of FIG. 20 is as shown in FIG. 21, and is comparable to the timing diagram of FIG. 17 with the addition that timings are applied to the voltage signal RSTL. Accordingly, RSTL may assume a voltage of VRST during the performing of the reset operation (i.e. when RST) is taken high, re-setting the voltage at the gate of sensing transistor 62 to VRST. Likewise RSTL may assume a voltage of VDD during the operation of the row select function (RWS high).

The sixth embodiment has all of the advantages of the fourth embodiment with the additional advantage that the array element circuit requires one fewer addressing lines in comparison to the array element circuit of the fourth embodiment. This may enable a smaller array element size with the same advantages as previously described.

Whilst in the preceding embodiments, the invention has been described in terms of an AM-EWOD device utilizing thin film electronics 74 to implement array element circuits and driver systems in thin film transistor (TFT) technology, the invention could equally be realized using other standard electronic manufacturing processes, e.g. Complementary Metal Oxide Semiconductor (CMOS), bipolar junction transistors (BJTs), and other suitable processes.

An aspect of the invention, therefore, is an active matrix electro-wetting on dielectric (AM-EWOD) device. In exemplary embodiments, the AM-EWOD device includes a plurality of array elements arranged in an array of rows and columns, each of the array elements including array element circuitry, an element electrode, and a reference electrode. The array element circuitry comprises an actuation circuit configured to apply actuation voltages to the element and reference electrodes for actuating the array element, and an impedance sensor circuit configured to sense impedance at the array element electrode to determine a droplet property at the array element. The actuation circuitry comprises a memory part including a memory capacitor for storing voltage data corresponding to either an actuated state or an unactuated state of the array element, and an input applied to the memory capacitor effects an operation of the impedance sensor circuit. The AM-EWOD device may include one or more of the following features, either individually or in combination.

In an exemplary embodiment of the AM-EWOD device, the AM-EWOD device further includes a row select line that is configured to provide an input to the memory capacitor, and the input from the row select line to the memory capacitor effects an operation of the impedance sensor circuit by operating so as to isolate the array element from the actuation voltage during the operation of the impedance sensor circuit.

In an exemplary embodiment of the AM-EWOD device, the AM-EWOD device further includes a transistor connected between an actuation signal and the element electrode and whose gate is connected to the memory capacitor, wherein the input from the row select line to the memory capacitor operates to turn off the transistor to isolate the array element from the actuation voltage during the operation of the impedance sensor circuit.

In an exemplary embodiment of the AM-EWOD device, the sensor circuit comprises a reference capacitor and a sensor capacitor, and the impedance sensor circuit is configured to operate by forming a potential divider circuit comprising the reference capacitor and the sensor capacitor.

In an exemplary embodiment of the AM-EWOD device, the memory capacitor acts as the reference capacitor.

In an exemplary embodiment of the AM-EWOD device, the AM-EWOD device further includes a row select line that provides an input to the reference capacitor, wherein an input from the row select line to the reference capacitor effects an operation of the impedance sensor circuit by perturbing a potential at the array element as part of operating the impedance sensor circuit, and the droplet property is determined based on an amount of change of the potential at the array element.

In an exemplary embodiment of the AM-EWOD device, the transistor connected between the memory capacitor and the impedance sensor circuit is a p-type transistor.

In an exemplary embodiment of the AM-EWOD device, the transistor connected between the memory capacitor and the impedance sensor circuit is an n-type transistor, and further comprising another row select line that provides an input to the n-type transistor. The row select line is connected to the reference capacitor, an input from the row select line to the reference capacitor perturbs the potential at the array element as part of operating the impedance sensor circuit, and an input from the another row select line to the n-type transistor is an inverse input of the input from the row select line to the reference capacitor.

In an exemplary embodiment of the AM-EWOD device, the impedance sensor circuit further comprises a capacitor connected between the element electrode and a gate of a sensing transistor, and the impedance at the array element is sensed based on a change in a sensing voltage coupled across the capacitor.

In an exemplary embodiment of the AM-EWOD device, the AM-EWOD device further includes a common addressing line that is connected to each of the two transistors for setting the sensing voltage at the gate of the sensing transistor and providing a bias supply to the drain of the sensing transistor.

In an exemplary embodiment of the AM-EWOD device, the AM-EWOD device further includes a sensor input line for actuating the impedance sensor circuit, and the memory capacitor operates as the reference capacitor in the operation of the impedance sensor circuit.

In an exemplary embodiment of the AM-EWOD device, the AM-EWOD device further includes a sensor input line for actuating the impedance sensor circuit. The memory capacitor operates as the reference capacitor in the operation of the impedance sensor circuit, and the actuating voltage for actuating the array element also is inputted to the one of the transistors of the impedance sensor circuit for resetting the sensing voltage.

In an exemplary embodiment of the AM-EWOD device, the actuator circuit further comprises two transistors for controlling the storing of the voltage data on the memory capacitor.

Another aspect of the invention is a method of operating an active matrix electro-wetting on dielectric (AM-EWOD) device. In exemplary embodiments, the operating method includes the steps of: arranging a plurality of array elements in an array of rows and columns, each of the array elements including array element circuitry, an element electrode, and a reference electrode, and the array element circuitry comprises an actuation circuit and an impedance sensor circuit; applying actuation voltages with the actuation circuit to the element and reference electrodes to actuate the array element; wherein the actuation circuitry comprises a memory part including a memory capacitor, the method further comprising for storing voltage data on the memory capacitor corresponding to either an actuated state or an unactuated state of the array element; applying an input to the memory capacitor that operates to effect an operation of the impedance sensor circuit; sensing impedance at the array element electrode with the impedance sensor circuit; and determining a droplet property at the array element based on the sensed impedance. The operating method may include one or more of the following features, either individually or in combination.

In an exemplary embodiment of the operating method, the AM-EWOD device further comprises a row select line that provides an input to the memory capacitor, the operating method further comprising providing the input from the row select line to the memory capacitor to effect an operation of the impedance sensor circuit by isolating the array element from the actuation voltage during the operation of the impedance sensor circuit.

In an exemplary embodiment of the operating method, the AM-EWOD device further comprises a transistor connected between an actuation signal and the element electrode and whose gate is connected to the memory capacitor, wherein the input from the first row select line to the memory capacitor operates to turn off the transistor to isolate the array element from the actuation voltage during the operation of the impedance sensor circuit.

In an exemplary embodiment of the operating method, the impedance sensor circuit comprises a reference capacitor and a sensor capacitor, and sensing the impedance at the array element electrode comprises forming a potential divider comprising the reference capacitor and the sensor capacitor.

In an exemplary embodiment of the operating method, the memory capacitor effects an operation of the impedance sensor circuit by operating as the reference capacitor in the operation of the impedance sensor circuit.

In an exemplary embodiment of the operating method, the row select line is connected to the reference capacitor, and sensing impedance at the array element electrode comprises: perturbing the potential at the array element with an input from the row select line to the reference capacitor; sensing an amount of perturbing of the potential at the array element electrode based on a change of impedance at the array element electrode; and determining a droplet property at the array element based on an amount of perturbing of the potential at the array element electrode.

In an exemplary embodiment of the operating method, the AM-EWOD device further comprises a sensor input line, the operating method further comprising actuating the impedance sensor circuit with an input to the sensor input line.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

Optionally the device may also be arranged such that embodiments of the invention may be utilized in just a part or sub-array of the entire device. Optionally some or all of the multiple different embodiments may be utilized in different rows columns or regions of the device.

INDUSTRIAL APPLICABILITY

The described embodiments could be used to provide an enhance AM-EWOD device. The AM-EWOD device could form a part of a lab-on-a-chip system. Such devices could be used in manipulating, reacting and sensing chemical, biochemical or physiological materials. Applications include healthcare diagnostic testing, material testing, chemical or biochemical material synthesis, proteomics, and tools for research in life sciences and forensic science.

What is claimed is:

1. An active matrix electro-wetting on dielectric (AM-EWOD) device comprising:
a plurality of array elements arranged in an array of rows and columns, each of the array elements including array element circuitry, an element electrode, and a reference electrode;
wherein the array element circuitry comprises an actuation circuit that applies actuation voltages to the element and reference electrodes for actuating the array element, and an impedance sensor circuit that senses impedance at the array element electrode to determine a droplet property at the array element; and
wherein the actuation circuitry comprises a memory part including a memory capacitor for storing voltage data corresponding to either an actuated state or an unactuated state of the array element, and an input signal applied to the memory capacitor effects an operation of the impedance sensor circuit;
the actuation circuit comprising a first transistor, the memory capacitor, and a second transistor; wherein:
a drain of the first transistor is connected to an input DATA line, a gate of the first transistor is connected to an input ENABLE line, and a source of the first transistor is connected to a gate of the second transistor;
the memory capacitor is connected between the gate of the second transistor and a row select line; and
a drain of the second transistor is connected to an input actuation signal, and a source of the second transistor is connected to the impedance sensor circuit and the element electrode.

2. The AM-EWOD device of claim 1, further comprising a row select line that provides the input signal to the memory capacitor, and the input signal from the row select line to the memory capacitor effects the operation of the impedance sensor circuit by operating so as to isolate the array element from the actuation voltage during the operation of the impedance sensor circuit.

3. The AM-EWOD device of claim 2, further comprising a transistor connected between the actuation voltage and the element electrode and whose gate is connected to the memory capacitor, wherein the input signal from the row select line to the memory capacitor operates to turn off the transistor to isolate the array element from the actuation voltage during the operation of the impedance sensor circuit.

4. The AM-EWOD device of claim 3, wherein the transistor connected between the memory capacitor and the impedance sensor circuit is a p-type transistor.

5. The AM-EWOD device of claim 1, wherein the impedance sensor circuit comprises a reference capacitor and a sensor capacitor, and the impedance sensor circuit operates by forming a potential divider circuit comprising the reference capacitor and the sensor capacitor, and an electrical load present at the array element electrode.

6. The AM-EWOD device of claim 5, wherein the memory capacitor acts as the reference capacitor.

7. The AM-EWOD device of claim 5, further comprising a row select line that provides an input signal to the reference capacitor, wherein the input signal from the row select line to the reference capacitor effects an operation of the impedance sensor circuit by perturbing a potential at the array element as part of operating the impedance sensor circuit, and the droplet property is determined based on an amount of change of the potential at the array element.

8. The AM-EWOD device of claim 7, wherein the transistor connected between the memory capacitor and the impedance sensor circuit is an n-type transistor, and further comprising another row select line that provides an input signal to the n-type transistor, wherein:

the row select line is connected to the reference capacitor;

an input signal from the row select line to the reference capacitor perturbs the potential at the array element as part of operating the impedance sensor circuit; and an input signal from the another row select line to the n-type transistor is an inverse input of the input signal from the row select line to the reference capacitor.

9. The AM-EWOD device of claim 5, wherein the impedance sensor circuit further comprises a capacitor connected between the element electrode and a gate of a sensing transistor, and the impedance at the array element is sensed based on a change in a sensing voltage that passes through the capacitor to the gate of the sensing transistor.

10. The AM-EWOD device of claim 9, further comprising a common addressing line that is connected to each of the two transistors for setting the sensing voltage at the gate of the sensing transistor.

11. The AM-EWOD device of claim 9, further comprising a sensor input line over which an actuation signal is provided for actuating the impedance sensor circuit, and the memory capacitor operates as the reference capacitor in the operation of the impedance sensor circuit.

12. The AM-EWOD device of claim 9, further comprising a sensor input line over which an actuation signal is provided for actuating the impedance sensor circuit, wherein:

the memory capacitor operates as the reference capacitor in the operation of the impedance sensor circuit; and the actuation voltage for actuating the array element also is inputted to the one of the transistors of the impedance sensor circuit for resetting the sensing voltage.

\* \* \* \* \*